United States Patent
Dinan et al.

(10) Patent No.: US 12,215,067 B2
(45) Date of Patent: Feb. 4, 2025

(54) CHEMICAL COMPOUNDS TARGETING THE EYE AND USE THEREOF IN THE TREATMENT OF EYE DISEASES

(71) Applicants: BIOPHYTIS, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); SORBONNE UNIVERSITE, Paris (FR)

(72) Inventors: Laurence Dinan, Dorchester (GB); René Lafont, Paris (FR); Pierre Dilda, Paris (FR); Serge Camelo, La Plaine Saint-Denis (FR); Valérie Fontaine, Savigny le Temple (FR); Christine Balducci, Saint Germain les Arpajon (FR); Elodie Monteiro, Saint Maur des Fossés (FR); Louis Guibout, Asnières-sur-Seine (FR); Mathilde Latil, Paris (FR); José-Alain Sahel, Paris (FR); Stanislas Veillet, Savigny sur Orge (FR)

(73) Assignees: BIOPHYTIS, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); SORBONNE UNIVERSITE, Paris (FR)

( * ) Notice: Subject to any disclaimer, the term of this patent is extended or adjusted under 35 U.S.C. 154(b) by 403 days.

(21) Appl. No.: 17/788,534

(22) PCT Filed: Dec. 22, 2020

(86) PCT No.: PCT/FR2020/052605
§ 371 (c)(1),
(2) Date: Jun. 23, 2022

(87) PCT Pub. No.: WO2021/130451
PCT Pub. Date: Jul. 1, 2021

(65) Prior Publication Data
US 2023/0089459 A1    Mar. 23, 2023

(30) Foreign Application Priority Data
Dec. 26, 2019  (FR) .................................. 1915598

(51) Int. Cl.
| | | |
|---|---|---|
| *C07C 211/21* | (2006.01) |
| *A61P 27/02* | (2006.01) |
| *C07D 207/06* | (2006.01) |
| *C07D 211/32* | (2006.01) |
| *C07D 265/30* | (2006.01) |
| *C07D 273/06* | (2006.01) |
| *C07D 307/36* | (2006.01) |

(52) U.S. Cl.
CPC ............ *C07C 211/21* (2013.01); *A61P 27/02* (2018.01); *C07D 207/06* (2013.01); *C07D 211/32* (2013.01); *C07D 265/30* (2013.01); *C07D 273/06* (2013.01); *C07D 307/36* (2013.01)

(58) Field of Classification Search
None
See application file for complete search history.

(56) References Cited

FOREIGN PATENT DOCUMENTS

| EP | 0030009 | 6/1981 |
|---|---|---|
| JP | 2012-097003 | 5/2012 |
| WO | 2004/011423 | 2/2004 |

OTHER PUBLICATIONS

International Search Report for PCT/FR2020/052605, mailed Apr. 14, 2021, 6 pages.
Written Opinion of the ISA for PCT/FR2020/052605, mailed Apr. 14, 2021, 8 pages.
Fuhrhop J-H et al., "Bolaform Amphiphiles With a Rigid Hydrophobic Bixin Core in Surfacemonolayers and Lipid Membranes", Langmuir, American Chemical Society, vol. 6, No. 2, Feb. 1, 1990, pp. 497-505.
Teruyuki Komatsu et al., "Solid Vesicle Membrane Made ofmeso—Tetrakis[(bixinylamino)-o-phenyl]porphyrins", Journal of the American Chemical Society, vol. 119, No. 48, Dec. 3, 1997 (Dec. 3, 1997), pp. 11660-11665.
Valerie Fontaine et al., "Norbixin Protects Retinal Pigmented Epithelium Cells and Photoreceptors against A2E-Mediated Phototoxicity In Vitro and In Vivo", PLOS ONE, vol. 11, No. 12, Dec. 16, 2016, p. e0167793.

*Primary Examiner* — Samantha L Shterengarts
(74) *Attorney, Agent, or Firm* — NIXON & VANDERHYE

(57) ABSTRACT

Disclosed is chemical compounds C that are derivatives of norbixin and have tropism for the eye, and are intended to be used in the treatment of eye diseases in mammals, in particular in the context of altering the retinal pigment epithelium and more particularly in the context of age-related macular degeneration (AMD) and Stargardt's disease.

20 Claims, 4 Drawing Sheets

[Fig. 1]
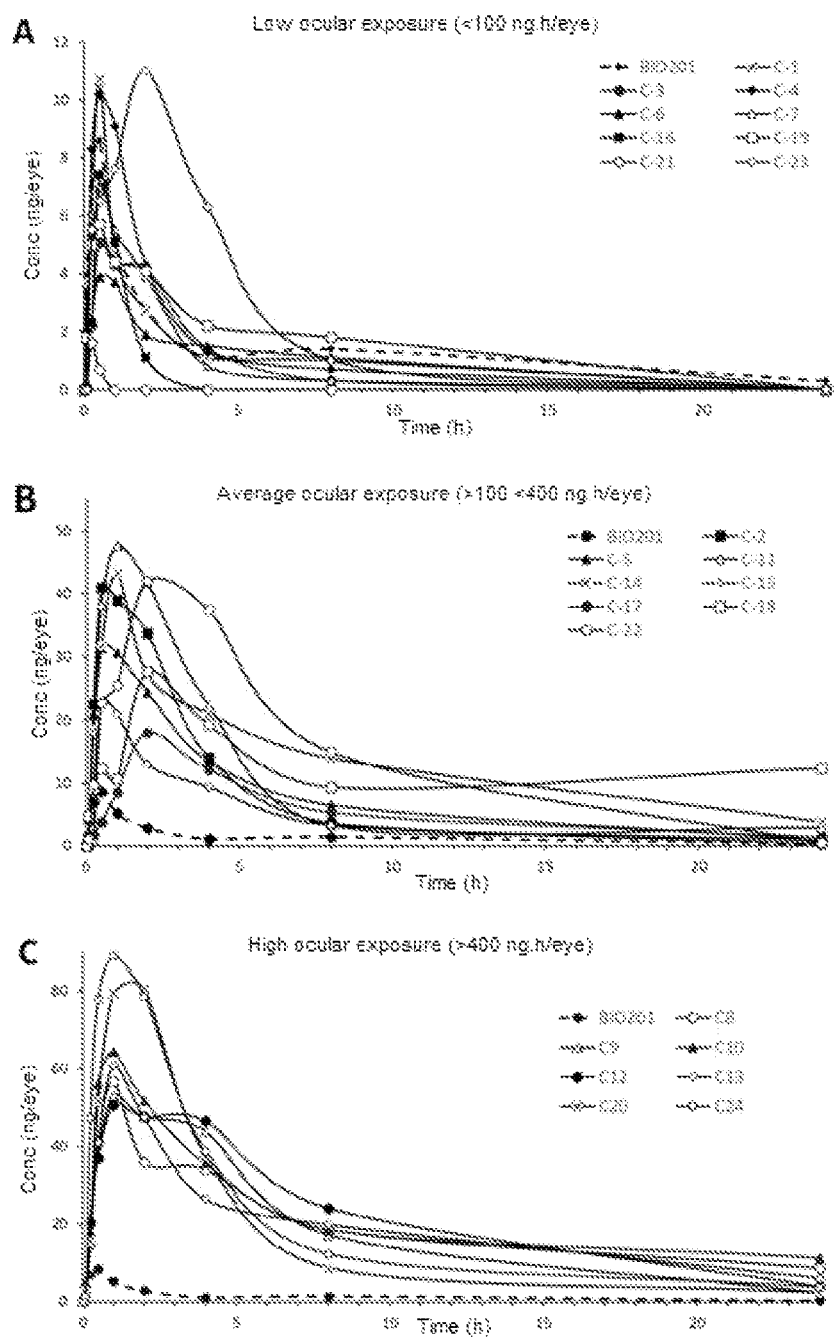

[Fig. 2]
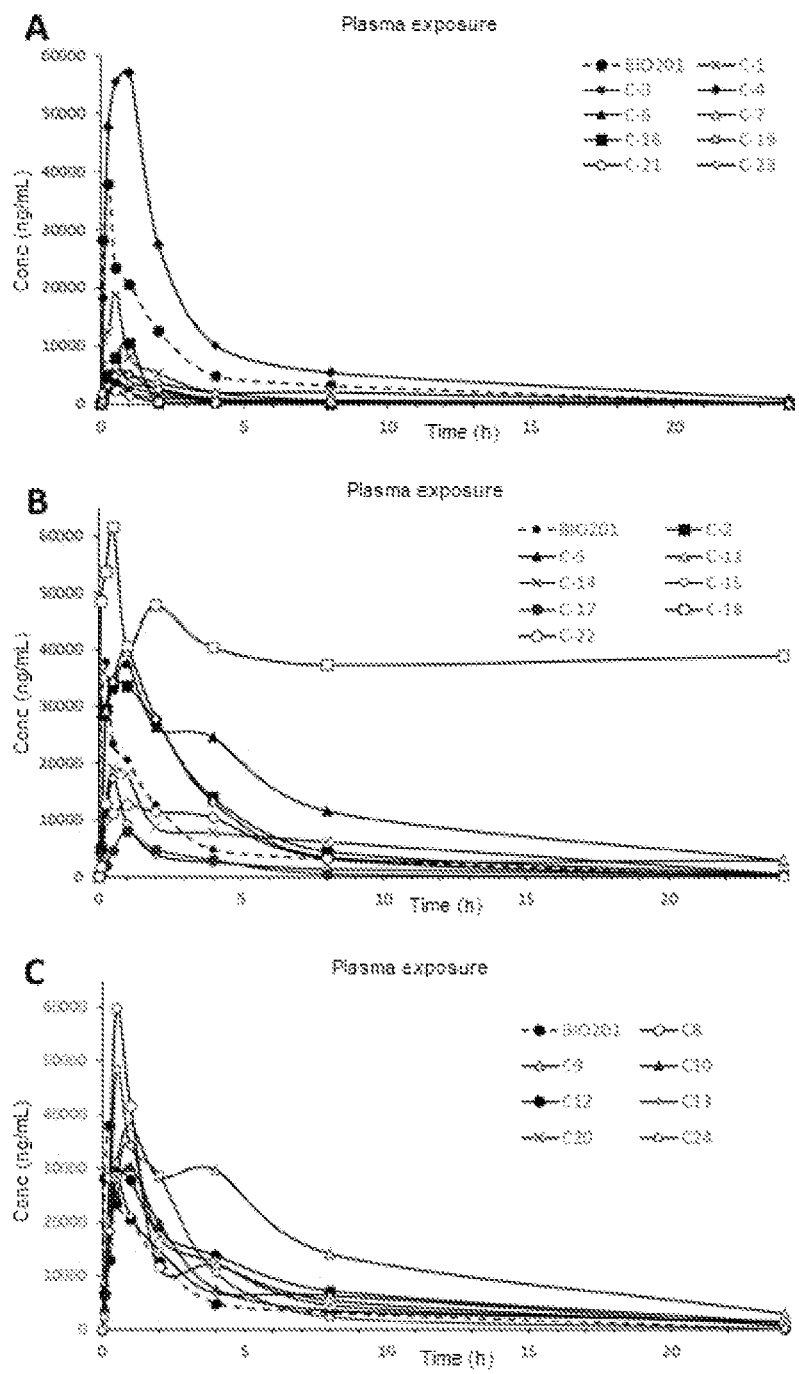

[Fig. 3]
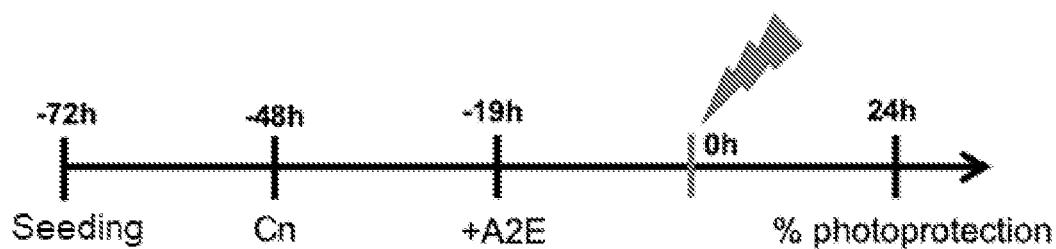

[Fig. 4]
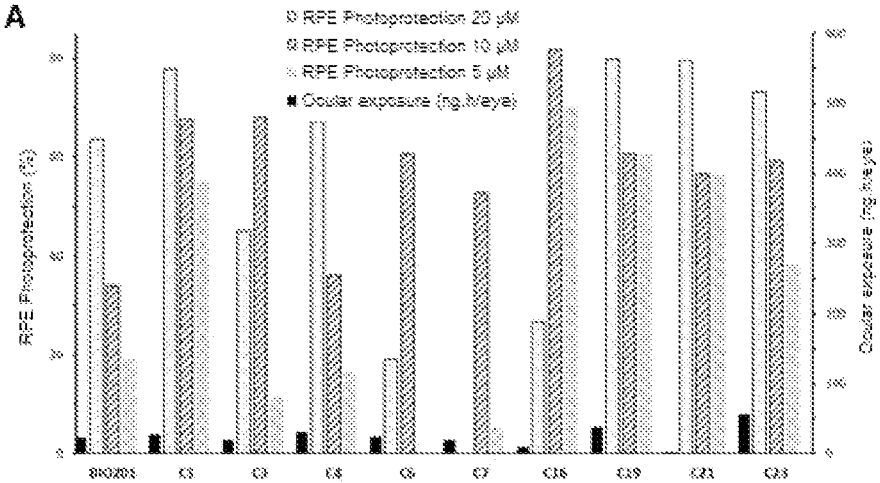
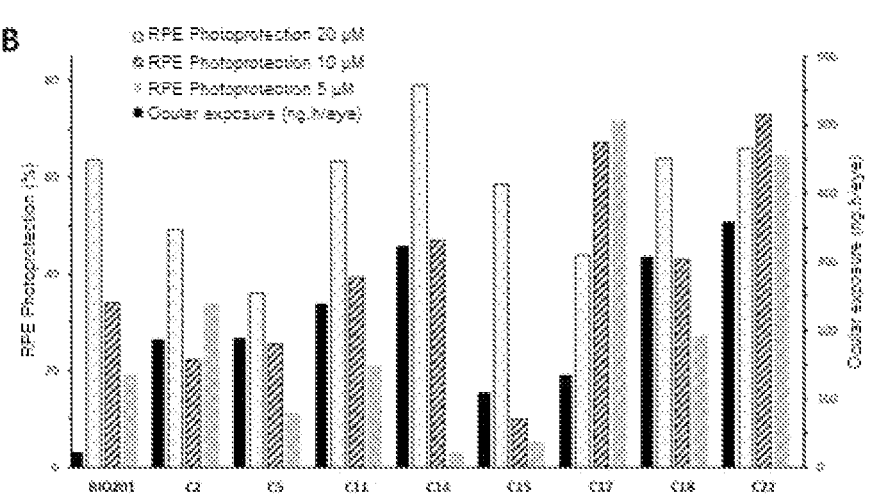
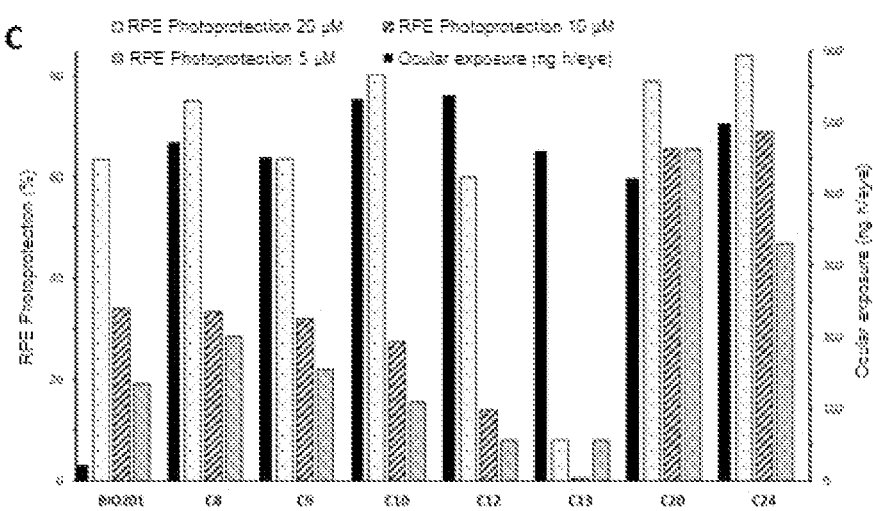

CHEMICAL COMPOUNDS TARGETING THE EYE AND USE THEREOF IN THE TREATMENT OF EYE DISEASES

CROSS-REFERENCE TO RELATED APPLICATIONS

This application is the U.S. national phase of International Application No. PCT/FR2020/052605 filed Dec. 22, 2020 which designated the U.S. and claims priority to Patent Application No. FR1915598 filed Dec. 26, 2019, the entire contents of each of which are hereby incorporated by reference.

BACKGROUND OF THE INVENTION

Field of the Invention

The invention relates to neo-synthesized chemical compounds having a tropism for the eye after an oral administration. It also relates to the field of therapeutic applications and relates to the use of said chemical compounds for improving vision in mammals.

More particularly, the present invention relates to the use of compounds for the protection of the cells of the retinal pigment epithelium (RPE), in particular for the treatment of age-related macular degeneration (AMD) or Stargardt's disease and Retinitis pigmentosa in mammals. The purpose of the invention is to improve the vision of the individuals afflicted with these diseases or at least stabilize the progress of these diseases.

Description of the Related Art

Age-related macular degeneration (AMD) is the most common cause of legal blindness in populations of persons aged 60 years or more, in particular in Europe and in North America (Smith et al. 2001). AMD affects the central portion of the retina, called macula, resulting in severe visual impairment and the irreversible loss of central vision.

The macular function is at the origin of central vision and of visual acuity of which the high resolution is linked to its high concentration in photoreceptors, specifically responsible for day vision and the perception of colors, and called cones. The early stage of AMD is marked by the appearance of deposits called Drusen, and by a progressive loss of the photoreceptors specialized in night vision called rods that affect day vision only marginally. However, little by little, the subject observes an alteration in their vision, which is then diagnosed by the ophthalmologist, this is the intermediate form or age-related macular degeneration (AMD). The later phases of AMD can have two forms, the wet form also called exudative or neo-vascular (characterized by the growth of choroidal neo-vessels in the subretinal space), or geographic atrophy (dry form) which is characterized by the loss of the cells of the retinal pigment epithelium (RPE) and of the photoreceptors which are the cells necessary for the visual cycle. The number of patients afflicted with intermediate AMD or the dry form is much more substantial than the number of subjects afflicted with the wet form of AMD (Smith et al. 2001). The last stages of AMD, regardless of its form (wet or dry) lead to the irreversible destruction of the macula. The progress of exudative AMD (wet form) can lead to complete blindness in a few weeks while the progress of dry AMD is generally slow.

Although the specific mechanisms involved in the initiation of AMD are multiple it has been shown that the oxidative stress and inflammation are important elements that contribute to its physiopathology. The etiological theories of AMD include hydrodynamic modifications in Bruch's membrane caused by a progressive accumulation of extracellular material containing lipids, and senescence of the RPE, of which the activity is indispensable for the survival of photoreceptors. The aging which is the first risk factor of AMD, causes a malfunction of the cells of the RPE and an insufficiency in their metabolism, as well as in their phagocytic activity. Incomplete digestion of the external segments of photoreceptors can lead to the formation of Drusen which reduce the diffusion through Bruch's membrane. With age, the RPE accumulates a growing quantity of lipofuscins. The latter are comprised of lipids and proteins, that come from phagolysosomes, lysosomes present in the cells of the RPE and directly from photoreceptors. Lipofuscins also contain N-retinyl-N-retinylidene ethanolamine (A2E), which is formed by the condensation of two molecules of retinaldehyde with one molecule of ethanolamine.

With age an increased accumulation of A2E in the retina of patients suffering from AMD is observed (Bhosale et al., 2009). Under the action of blue light and in the presence of oxygen, the A2E generates reactive species which cause damage to proteins, lipids and DNA, and therefore a substantial oxidative stress in the aging cells of the RPE (Sparrow & Cai, 2001). This damage disturbs the lysosomal activity of cells of the RPE and causes an accumulation of waste, which ends up by generating, from place to place, the death of the cells of the RPE which is followed by that of the photoreceptors with which they were associated.

Stargardt's disease and Retinitis pigmentosa are retinal degenerations of genetic origin that can be caused by a large number of mutations or genetic polymorphisms. These two pathologies can be likened to the dry form of AMD since they are characterized by a progressive loss of the cells of the RPE and of the photoreceptors which is linked to a progressive accumulation of A2E in the case of Stargardt's disease. As with the dry form of AMD, the degeneration of the photoreceptors and of the RPE, lead to a loss of night vision, then tardily of the central vision by patients afflicted with these two genetic pathologies.

Among the existing treatments intravitreal injections of anti-VEGF (Vascular Endothelial Growth Factor) antibodies are known which make it possible to partially block the formation of neo-vessels and thus offer a therapeutic option for the wet form of AMD. Currently there is no treatment on the market for the dry form of AMD (AMD and geographic atrophy). Likewise, currently no drug is available for the treatment of Stargardt's disease or Retinitis pigmentosa. In the framework of dry AMD food supplements have been formulated with generic antioxidant compounds, namely minerals and vitamins with antioxidant properties, for example zinc, vitamins A, C, and E. Their therapeutic efficacy is real but limited to AMD. Nutraceuticals 1 and 2 AREDS formulas ("Age-Related Eye Disease Study", AREDS 2001) are considered as the care standard in the United States for the treatment of AMD, reducing the risk of progressing to wet AMD by 25% and the loss of vision by 19% over five years. Many products propose a common formulation base: zinc and vitamins C and E, to which are added various ingredients: lutein, resveratrol, omega 3 fatty acids, without however having any convincing efficacy data on these additional ingredients, or on the categories of patients able to favorably respond to these different molecules (Elliot & Williams, 2012).

Carotenoids (molecules exclusively from food intake) were more particularly studied, because some of them (lutein, zeaxanthin=xanthophylls) are naturally present in the macula (Subczynski et al., 2010), and it is known that these compounds have a strong antioxidant power and also absorb blue light thus limiting its toxic effects. It is therefore logical that these compounds were tested (alone or in a combination) in AREDS formulas. The results obtained were disappointing, the supplementation was effective only for a subset of patients deficient in these compounds (Pinazo-Durán et al., 2014). Other xanthophylls were also the object of studies by oral supplementation, alone or in a combination with lutein and/or zeaxanthin (ex. astaxanthin—Parisi et al., 2008). Di-apo-carotenoids (=carotenoids truncated at both ends–IUPAC chemical nomenclature) were tested in vitro and in vivo, in particular crocetin (=8,8'-diapocarotene-8,8'-dioate) and the glycosides thereof (crocins). Crocins have a photo-protective effect in vitro on primary cultures of photoreceptors of cattle or of primates (Laabich et al., 2006), and crocetin protects the neuro-ganglionnar cells against oxidative stress (Yamauchi et al., 2011). Experiments were also conducted with another apo-carotenoid, bixin (=6-methylhydrogen [9Z] 6,6'-diapocarotene-6,6'-dioate) or some of the derivatives thereof, in vitro on neuro-ganglionnar cells and in vivo by intravitreal injections to counteract the effects of a stress of the endoplasmic reticulum (Tsuruma et al., 2012). A Urucum seed extract (*Bixa orellana*) previously developed (Bixilia®) enriched with bixin has shown a photo-protective effect on human skin exposed to UV (WO2010149942; Veillet et al., 2009) and on RPE cells subjected to a photo-oxidative stress (WO2012156600; Fontaine et al., 2011). Finally, norbixin (6,6'-diapocarotene-6,6'-dioate) and in particular its form 9'-cis, makes it possible to substantially reduce cell death caused by an illumination with blue radiation of the cells of the RPE pretreated with N-retinyl-N-retinylidene ethanolamine (A2E) (WO2016174360; Lafont et al. 2015, Fontaine et al. 2016). An oral chronic treatment with 9'-cis norbixin also makes it possible to decrease the accumulation of A2E in the retina of double KO mice (ABCA4$^{-/-}$, RDH8$^{-/-}$) (Fontaine et al. 2016). Although norbixin has good bioavailability its accumulation in the eye remains very low and therefore limits its protective activity of the retina.

SUMMARY OF THE INVENTION

The inventors have created innovative compounds by hemisynthesis. They have also discovered that some of these compounds have a better pharmacokinetic profile and a better tropism for the eye than those of norbixin. In addition, some of these compounds have a photo-protective activity of the retinal pigment epithelium (RPE) that is equivalent or superior to that of norbixin.

According to a first aspect, the invention therefore proposes a chemical compound having the following general formula (I):

[Chem. 1]

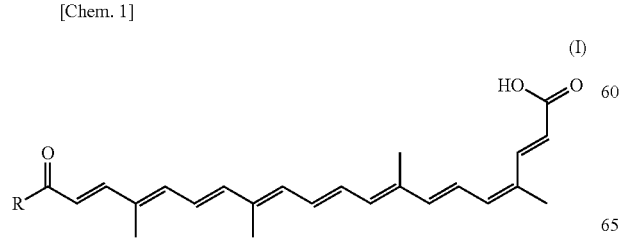

(I)

where COR is a secondary or tertiary amide, such that —R is chosen from:

-M; —NH—(CH$_2$)$_n$-M and —NH—(CH$_2$)$_n$—C(CH$_3$)(CH$_3$)-M, -M being chosen from a)

[Chem. 2]

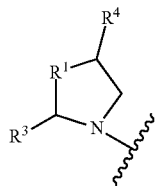

[Chem. 3]

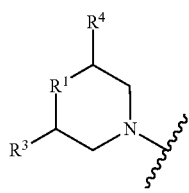

[Chem. 4]

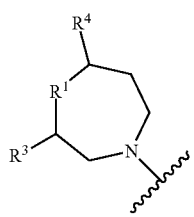

wherein,

R$^1$ is chosen from an oxygen atom, a sulfur atom, a >CH$_2$, >CH—O—(CH$_2$)$_n$—CH$_3$, >CH—(CH$_2$)$_n$—O—(CH$_2$)$_n$—CH$_3$, >CH—(CH$_2$)$_n$—OH, >CH—COOH, >C(OH)phenyl or >NH group;

R$^3$ is chosen from a hydrogen atom, a C$_1$-C$_6$ alkyl, —OH or C$_1$-C$_6$ —O-alkyl group;

R$^4$ is chosen from a hydrogen atom, a C$_1$-C$_6$ alkyl, —OH or C$_1$-C$_6$ —O-alkyl group;

n is an integer comprised between 0 and 6;

—NH—(CH$_2$)$_n$—W, W being a hydrogen atom, or a —OH group, a —O—(CH$_2$)$_n$—CH$_3$ group, or a group chosen from i)

[Chem. 5]

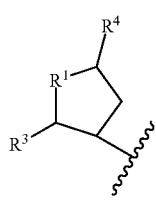

-continued

[Chem. 6]

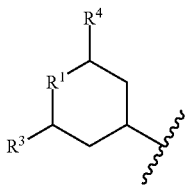

[Chem. 7]

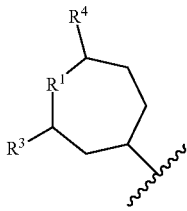

[Chem. 8]

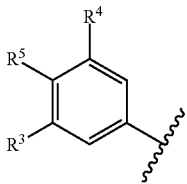

[Chem. 9]

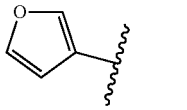

wherein,
- $R^1$ is chosen from an oxygen atom, a sulfur atom, a >$CH_2$, >CH—O—$(CH_2)_n$—$CH_3$, >CH—$(CH_2)_n$—OH, >CH—COOH, >C(OH)phenyl or >NH group;
- $R^3$ is chosen from a hydrogen atom, a $C_1$-$C_6$ alkyl, —OH or $C_1$-$C_6$ —O-alkyl group;
- $R^4$ is chosen from a hydrogen atom, a $C_1$-$C_6$ alkyl, —OH or $C_1$-$C_6$ —O-alkyl group;
- $R^5$ is chosen from a —$CH_3$, —OH, —O—$(CH_2)_n$—$CH_3$, —$(CH_2)_n$—OH or —COOH group;
- n is an integer comprised between 0 and 6;

as well as the pharmaceutically acceptable salts of said chemical compound.

The term "chemical compound" also means the isomers of said chemical compound and in particular the stereoisomers.

In the framework of the present invention "pharmaceutically acceptable" means that which is useful in the preparation of a pharmaceutical composition which is generally safe, non-toxic and that is not biologically or otherwise undesirable and which is acceptable for veterinary use as well as a human pharmaceutical.

In the framework of the present invention the term "pharmaceutically acceptable salts of a compound" means salts which are pharmaceutically acceptable, as defined here, and which have the desired pharmacological activity of the parent compound. Such salts include:

(1) acid addition salts formed with mineral acids such as hydrochloric acid, hydrobromic acid, sulfuric acid, nitric acid, phosphoric acid and similar; or formed with organic acids such as acetic acid, benzenesulfonic acid, benzoic acid, camphor-sulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and similar; or (2) the salts formed when an acidic proton present in the parent compound is either replaced with a metal ion, for example an alkali metal ion, an alkaline earth metal ion or an aluminum ion; or coordinates with an organic or inorganic base. Acceptable organic bases include diethanolamine, ethanolamine, N-methylglucamine, triethanolamine, tromethamine and similar. Acceptable inorganic bases include aluminum hydroxide, calcium hydroxide, potassium hydroxide, sodium carbonate and sodium hydroxide. According to a particular embodiment, the invention relates to a chemical compound having the general formula (I) chosen from the following chemical compounds:

1-[2-methoxyethanamido](2E,4E,6E,8E,10E,12E,14E,16Z,18E)-4,8,13,17-tetramethylicosa-2,4,6,8,10,12,14,16,18-nonaenedioate;

1-[1,4-oxazinamido](2E,4E,6E,8E,10E,12E,14E,16Z,18E)-4,8,13,17-tetramethylicosa-2,4,6,8,10,12,14,16,18-nonaenedioate;

1-[piperidinamido](2E,4E,6E,8E,10E,12E,14E,16Z,18E)-4,8,13,17-tetramethylicosa-2,4,6,8,10,12,14,16,18-nonaenedioate;

1-[2-hydoxyethanamido](2E,4E,6E,8E,10E,12E,14E,16Z,18E)-4,8,13,17-tetramethylicosa-2,4,6,8,10,12,14,16,18-nonaenedioate;

1[1,4-oxazepanamido](2E,4E,6E,8E,10E,12E,14E,16Z,18E)-4,8,13,17-tetramethylicosa-2,4,6,8,10,12,14,16,18-nonaenedioate;

1-thiomorpholinamido-(2E,4E,6E,8E,10E,12E,14E,16Z,18E)-4,8,13,17-tetramethylicosa-2,4,6,8,10,12,14,16,18-nonaenedioate;

1-pyrrolidinamido-(2E,4E,6E,8E,10E,12E,14E,16Z,18E)-4,8,13,17-tetramethylicosa-2,4,6,8,10,12,14,16,18-nonaenedioate;

1-[2-morpholinopropanamido](2E,4E,6E,8E,10E,12E,14E,16Z,18E)-4,8,13,17-tetramethylicosa-2,4,6,8,10,12,14,16,18-nonaenedioate;

1-[(S)-3-hydroxypyrrolidinamido](2E,4E,6E,8E,10E,12E,14E,16Z,18E)-4,8,13,17-tetramethylicosa-2,4,6,8,10,12,14,16,18-nonaenedioate;

1-[2-morpholinoethanamido](2E,4E,6E,8E,10E,12E,14E,16Z,18E)-4,8,13,17-tetramethylicosa-2,4,6,8,10,12,14,16,18-nonaenedioate;

1-[(R)-3-hydroxypyrrolidinamido](2E,4E,6E,8E,10E,12E,14E,16Z,18E)-4,8,13,17-tetramethylicosa-2,4,6,8,10,12,14,16,18-nonaenedioate;

1-[4-hydroxypiperidinamido](2E,4E,6E,8E,10E,12E,14E,16Z,18E)-4,8,13,17-tetramethylicosa-2,4,6,8,10,12,14,16,18-nonaenedioate;

1-[2-methyl-2-(4-morpholinyl)propylamido](2E,4E,6E,8E,10E,12E,14E,16Z,18E)-4,8,13,17-tetramethylicosa-2,4,6,8,10,12,14,16,18-nonaenedioate;

1-[4-hydroxymethylpiperidinamido](2E,4E,6E,8E,10E,12E,14E,16Z,18E)-4,8,13,17-tetramethylicosa-2,4,6,8,10,12,14,16,18-nonaenedioate;

1-[(Z)-2,6-dimethylmorpholinamido](2E,4E,6E,8E,10E,12E,14E,16Z,18E)-4,8,13,17-tetramethylicosa-2,4,6,8,10,12,14,16,18-nonaenedioate;

1-[4-hydroxyphenylamido](2E,4E,6E,8E,10E,12E,14E,
16Z,18E)-4,8,13,17-tetramethylicosa-2,4,6,8,10,12,14,
16,18-nonaenedioate;
1-[4-benzyl-4-hydroxypiperidinamido](2E,4E,6E,8E,10E,
12E,14E,16Z,18E)-4,8,13,17-tetramethylicosa-2,4,6,8,
10,12,14,16,18-nonaenedioate;
1-[4-carboxypiperidinamido](2E,4E,6E,8E,10E,12E,14E,
16Z,18E)-4,8,13,17-tetramethylicosa-2,4,6,8,10,12,14,
16,18-nonaenedioate;
1-[(E)-4-hydroxycyclohexamido](2E,4E,6E,8E,10E,12E,
14E,16Z,18E)-4,8,13,17-tetramethylicosa-2,4,6,8,10,12,
14,16,18-nonaenedioate;
1-[3-methoxypiperidinamido](2E,4E,6E,8E,10E,12E,14E,
16Z,18E)-4,8,13,17-tetramethylicosa-2,4,6,8,10,12,14,
16,18-nonaenedioate;
1-[4-methoxypiperidinamido](2E,4E,6E,8E,10E,12E,14E,
16Z,18E)-4,8,13,17-tetramethylicosa-2,4,6,8,10,12,14,
16,18-nonaenedioate;
1-[2-(2-furyl)ethanamido](2E,4E,6E,8E,10E,12E,14E,16Z,
18E)-4,8,13,17-tetramethylicosa-2,4,6,8,10,12,14,16,18-
nonaenedioate;
1-[4-n-propoxypiperidinamido](2E,4E,6E,8E,10E,12E,14E,
16Z,18E)-4,8,13,17-tetramethylicosa-2,4,6,8,10,12,14,
16,18-nonaenedioate;
1-[4-ethylmethoxypiperidinamido](2E,4E,6E,8E,10E,12E,
14E,16Z,18E)-4,8,13,17-tetramethylicosa-2,4,6,8,10,12,
14,16,18-nonaenedioate.

According to a second aspect, the present invention relates to a composition including at least one chemical compound object of the present invention.

According to a particular embodiment of the present invention, the composition comprises at least one excipient. Examples of excipients are fillers, diluents, disintegrants, lubricants, preservatives, disintegrators, sweetener, etc. According to a particular example, at least one excipient is chosen from an oil, water and an alcohol, a silicone.

According to a particular embodiment of the present invention, the composition comprises a support in a form adapted to be ingested, injected into the eye or injected into the blood According to a third aspect the present invention relates to a chemical compound having the general formula (I) or the composition including at least one chemical compound having the general formula (I) for the use thereof as a drug.

According to an embodiment the invention relates to the chemical compound having the general formula (I) or the composition including at least one chemical compound having the general formula (I) for the use thereof for the treatment and/or the prevention of damage to the retina of mammals caused by retinal degenerations.

According to an embodiment the invention relates to the chemical compound having the general formula (I) or the composition including at least one chemical compound having the general formula (I) for the use thereof for the photoprotection of the cells of the retinal pigment epithelium in mammals.

According to an embodiment the invention relates to the chemical compound having the general formula (I) or the composition including at least one chemical compound having the general formula (I) for the use thereof for the prevention of damage to the retina of mammals caused by exposure to blue light corresponding to the blue band of the visible light spectrum, of a wavelength comprised between 435 nm and 490 nm.

According to an embodiment the invention relates to the chemical compound having the general formula (I) or the composition including at least one chemical compound having the general formula (I) for the use thereof in the treatment and/or the prevention of eye diseases in mammals.

According to an embodiment the invention relates to the chemical compound having the general formula (I) or the composition including at least one chemical compound having the general formula (I) for the use thereof in the treatment and/or the prevention of retinopathies in mammals.

According to an embodiment the invention relates to the chemical compound having the general formula (I) or the composition including at least one chemical compound having the general formula (I) for the use thereof in the treatment and/or the prevention of age-related macular degeneration (AMD) in mammals. The chemical compound object of the present invention advantageously makes it possible to improve the vision of the individuals afflicted with this disease or at least stabilize the progress of the disease.

According to another embodiment the invention relates to the chemical compound having the general formula (I) or the composition including at least one chemical compound having the general formula (I) for the use thereof in the treatment and/or the prevention of Stargardt's disease and Retinitis pigmentosa in mammals. The chemical compound object of the present invention advantageously makes it possible to improve the vision of the individuals afflicted with these diseases.

BRIEF DESCRIPTION OF THE DRAWINGS

The invention shall be better understood when reading the following description, given as an example and in no way limiting, and given in reference to the figures which show:

FIG. 1 shows pharmacokinetic profiles of compounds object of the present invention in the eye. These are graphs showing the ocular concentrations as a function of time after administration of the Chemical compounds (C) object of the present invention and of norbixin (BIO201). All the compounds were administered by mouth (p.o.) at 50 mg/kg formulated in a medium D-α-Tocopheryl polyethylene glycol 1000 succinate (VitE-TPGS) 20% in a sodium bicarbonate buffer (0.1M). The pharmacokinetic profiles of compounds having a low ocular exposure are shown in the graph A of FIG. 1, those having an average ocular exposure are shown in the graph B of FIG. 1, and those having a high ocular exposure are shown in the graph C of FIG. 1.

FIG. 2 shows pharmacokinetic profiles of compounds object of the present invention in the plasma. These are graphs showing the plasma concentrations as a function of time after administration of the Compounds (C) and norbixin (BIO201). All the compounds were administered by mouth (p.o.) at 50 mg/kg formulated in a medium VitE-TPGS 20% in a sodium bicarbonate buffer (0.1M). The plasma exposure profiles of compounds having a low ocular exposure are shown in the graph A of FIG. 2, those of the compounds having an average ocular exposure are shown in the graph B of FIG. 2, and finally those of the compounds having a high ocular exposure are shown in the graph C of FIG. 2.

FIG. 3 shows a chronogram of the photoprotection experiments of the cells of the retinal pigment epithelium (RPE) by compounds (C) object of the present invention in vitro. This is the chronology of the steps implemented so as to test the photo-protective activity of the various chemical compounds (C) compared to that of native norbixin on the cells of the RPE put into the presence of A2E and subjected to an illumination.

FIG. 4 shows the targeting of the eye and the percentage of photoprotection in vitro of the compounds object of the present invention. These are histograms showing in a combined manner the areas under the curve of the ocular concentrations (ocular exposure) of norbixin (BIO201) and of various compounds C object of the present invention, and the percentages of photoprotection obtained with norbixin and the compounds object of the present invention at 5 µM, 10 µM and 20 µM. The compounds having a low ocular exposure are shown in histogram A, those having an average ocular exposure are shown in histogram B, and those having a high ocular exposure are shown in histogram C.

DESCRIPTION OF THE PREFERRED EMBODIMENTS

The chemical compounds object of the present invention do not exist in the chemical databases of carotenoids and di-apo-carotenoids. They are synthesized according to processes that can be industrialized, i.e. with a minimum of synthesis steps and an optimum yield. They have a better pharmacokinetic profile and a better tropism for the eye than those of norbixin. Some of these compounds moreover have a photo-protective activity of the RPE superior than that of norbixin.

Description of Syntheses and General Diagrams

The chemical compounds having general formula (I):

[Chem. 1]

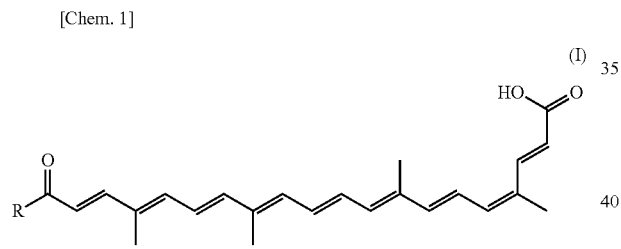

can be prepared by application or adaptation of any method known per se to a person skilled in the art and/or within the scope of the latter, which have been able to be described, or by application or adaptation of methods described in the following procedures.

In the description that follows the various groups refer to the definitions given hereinabove, i.e.:

COR is a secondary or tertiary amide, such that —R is chosen from:

-M; —NH—(CH$_2$)$_n$-M and —NH—(CH$_2$)$_n$—C(CH$_3$)(CH$_3$)-M, -M being chosen from a)

[Chem. 2]

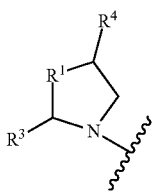

-continued

[Chem. 3]

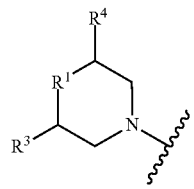

[Chem. 4]

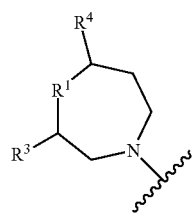

wherein,

R$^1$ is chosen from an oxygen atom, a sulfur atom, a >CH$_2$, >CH—O—(CH$_2$)$_n$—CH$_3$, >CH—(CH$_2$)$_n$—O—(CH$_2$)$_n$—CH$_3$, >CH—(CH$_2$)$_n$—OH, >CH—COOH, >C(OH)phenyl or >NH group;

R$^3$ is chosen from a hydrogen atom, a C$_1$-C$_6$ alkyl, —OH or C$_1$-C$_6$ —O-alkyl group;

R$^4$ is chosen from a hydrogen atom, a C$_1$-C$_6$ alkyl, —OH or C$_1$-C$_6$ —O-alkyl group;

n is an integer comprised between 0 and 6;

—NH—(CH$_2$)$_n$—W, W being a hydrogen atom, or a —OH group, a —O—(CH$_2$)$_n$—CH$_3$ group, or a group chosen from i)

[Chem. 5]

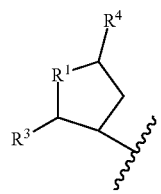

[Chem. 6]

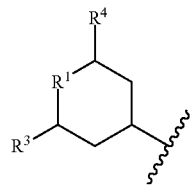

[Chem. 7]

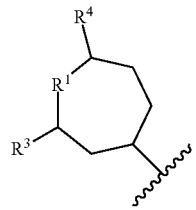

-continued

[Chem. 8]

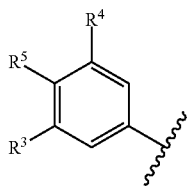

[Chem. 9]

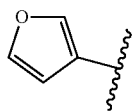

wherein,

R$^1$ is chosen from an oxygen atom, a sulfur atom, a >CH$_2$, >CH—O—(CH$_2$)$_n$—CH$_3$, >CH—(CH$_2$)$_n$—OH, >CH—COOH, >C(OH)phenyl or >NH group;

R$^3$ is chosen from a hydrogen atom, a C$_1$-C$_6$ alkyl, —OH or C$_1$-C$_6$ —O-alkyl group;

R$^4$ is chosen from a hydrogen atom, a C$_1$-C$_6$ alkyl, —OH or C$_1$-C$_6$ —O-alkyl group;

R$^5$ is chosen from a —CH$_3$, —OH, —O—(CH$_2$)$_n$—CH$_3$, —(CH$_2$)$_n$—OH or —COOH group;

n is an integer comprised between 0 and 6.

In the framework of the present invention the term "C$_1$-C$_6$ alkyl group" means any alkyl group with 1 to 6 carbon atoms, linear or branched, in particular, the methyl, ethyl, n-propyl, iso-propyl, n-butyl, iso-butyl, sec-butyl, t-butyl, n-pentyl, n-hexyl groups. Advantageously it is a methyl, ethyl, iso-propyl or t-butyl group, in particular a methyl or ethyl group, more particularly a methyl group.

Diagram A for the synthesis of the compound 1-[2-(2-furyl)ethanamido](2E,4E,6E,8E,10E,12E,14E,16Z,18E)-4,8,13,17-tetramethylicosa-2,4,6,8,10,12,14,16,18-nonaenedioate (called compound C21):

Formation of Amide (First Method)

[Chem. 10]

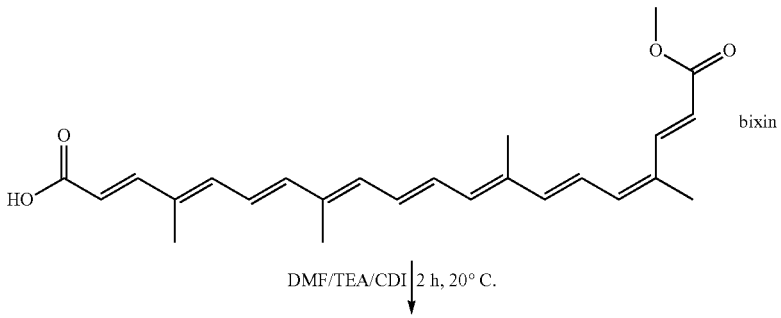

bixin

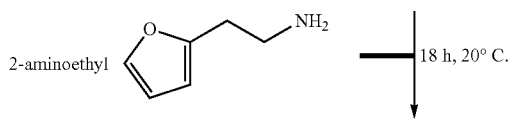

2-aminoethyl

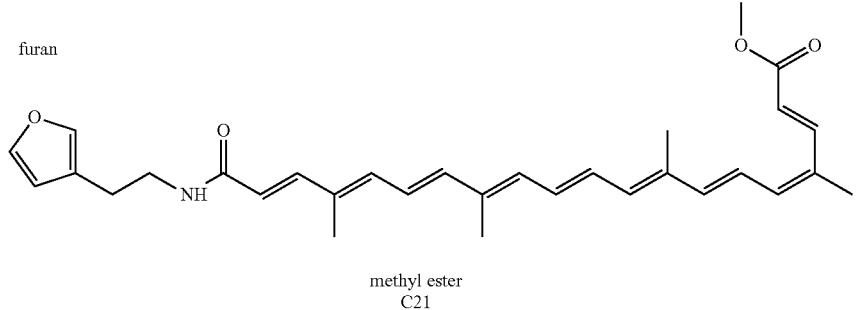

furan methyl ester
C21

Hydrolysis of Methyl Ester
[Chem. 11]
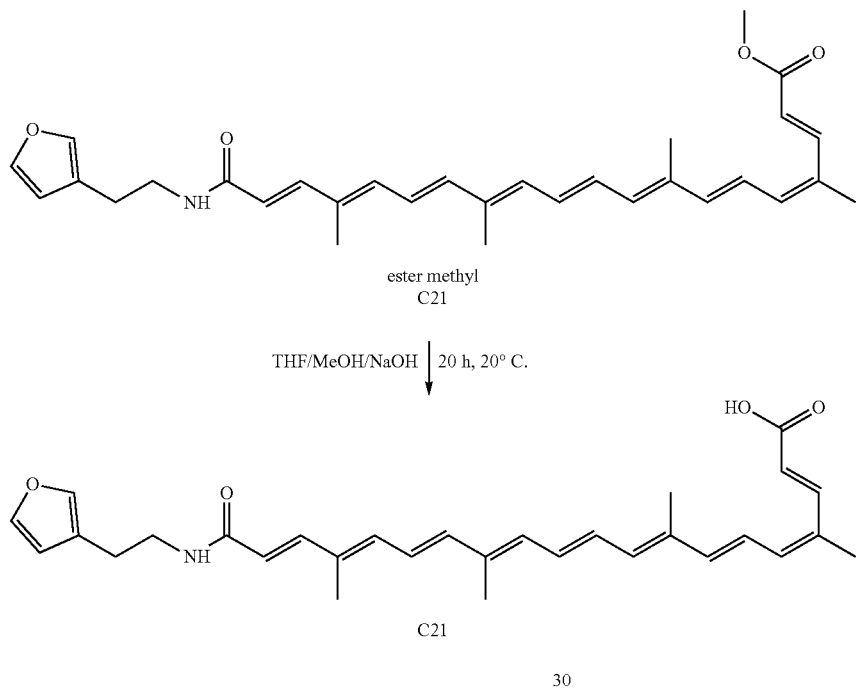
ester methyl C21
THF/MeOH/NaOH  20 h, 20° C.
C21
30
Diagram B for the synthesis of the compound 1-[(E)-4-hydroxycyclohexamido](2E,4E,6E,8E,10E,12E,14E,16Z,18E)-4,8,13,17-tetramethylicosa-2,4,6,8,10,12,14,16,18-nonaenedioate (called compound C19: Formation of Amide (Second Method)
[Chem. 12]
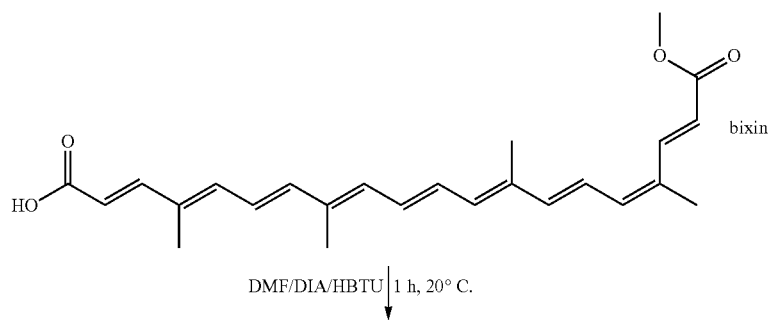
bixin
DMF/DIA/HBTU  1 h, 20° C.
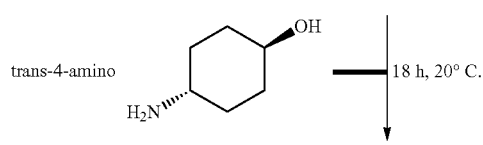
trans-4-amino
18 h, 20° C.

-continued

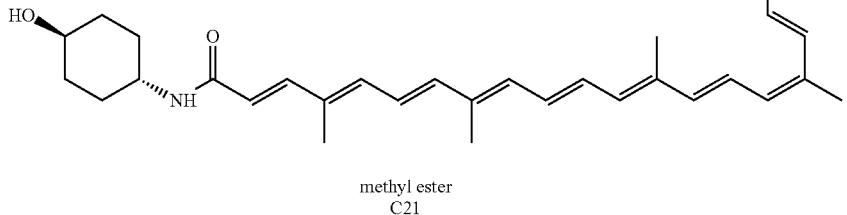

cyclohexanol
methyl ester
C21

DMF=dimethylformamide
TEA=triethylamine
DIA=diisopropylamine
THF=tetrahydrofuran
CDI=carbonyldiimidazole
HBTU=(1H-benzotriazol-1-yloxy)(dimethylamino)-N,N-dimethylmethaniminium hexafluorophosphate

EXAMPLES

Equipment and Methods

The nuclear magnetic resonance (NMR) spectra of the proton ($^1$H) are carried out on a Bruker Avance DPX500 device (500, 0.7 MHz). The chemical shifts (δ) are measured in parts per million (ppm). The spectra are calibrated on the chemical shift of the deuterated solvent used. The coupling constants (J) are expressed in Hertz (Hz) and the multiplicity is represented in the following way, singlet (s), doublet (d), doublet of doublet (dd), triplet (t), triplet of doublet (td), quadruplet (q), multiplet (m). The mass spectra (MS) are carried out with an Agilent Technologies MSD spectrometer, G1946A type, the samples are ionized by an "Atmospheric pressure chemical ionization" (APCI) source.

By way of illustrating examples of the invention, the molecules shown in table 1 were synthesized.

TABLE 1

| No | Chemical structure | Chemical name |
|----|-------------------|---------------|
| C1 | 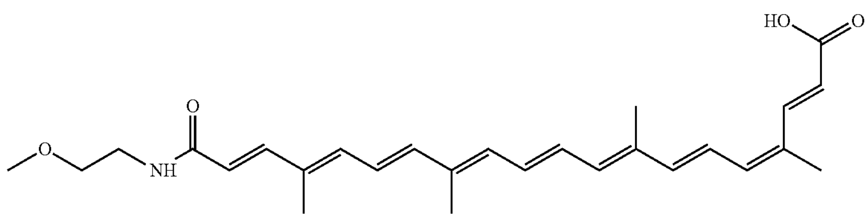 [SMILES: COCCNC(=O)/C=C/C(C)=C/C=C/C(C)=C/C=C/C=C(C)/C=C/C=C(C)\C=C\C(=O)O] | 1-[2-methoxyethanamido](2E,4E,6E,8E,10E,12E,14E,16Z,18E)-4,8,13,17-tetramethylicosa-2,4,6,8,10,12,14,16,18-nonaenedioate |
| C2 | 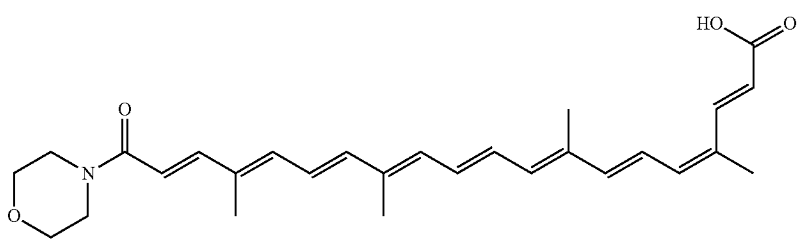 [SMILES: CC(=C/C=C/C(C)=C/C=C/C=C(C)/C=C/C=C(C)/C=C/C(=O)N1CCOCC1)/C=C/C(=O)O] | 1-[1,4-oxazinamido](2E,4E,6E,8E,10E,12E,14E,16Z,18E)-4,8,13,17-tetramethylicosa-2,4,6,8,10,12,14,16,18-nonaenedioate |
| C3 | 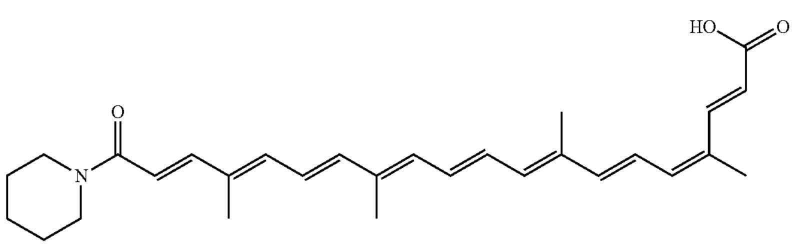 [SMILES: CC(=C/C=C/C(C)=C/C=C/C=C(C)/C=C/C=C(C)/C=C/C(=O)N1CCCCC1)/C=C/C(=O)O] | 1-[piperidinamido](2E,4E,6E,8E,10E,12E,14E,16Z,18E)-4,8,13,17-tetramethylicosa-2,4,6,8,10,12,14,16,18-nonaenedioate |

TABLE 1-continued

| No | Chemical structure | Chemical name |
|---|---|---|
| C4 | 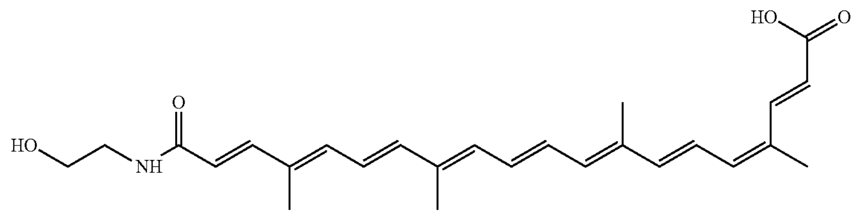 [SMILES: CC(=C/C=C/C(C)=C/C=C/C=C(C)/C=C/C=C(C)/C=C/C(=O)NCCO)/C=C/C(=O)O] | 1-[2-hydroxyethanamido](2E,4E,6E,8E,10E,12E,14E,16Z,18E)-4,8,13,17-tetramethylicosa-2,4,6,8,10,12,14,16,18-nonaenedioate |
| C5 | 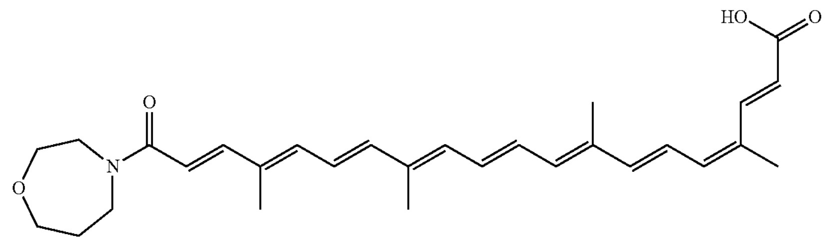 [SMILES: CC(=C/C=C/C(C)=C/C=C/C=C(C)/C=C/C=C(C)/C=C/C(=O)N1CCCOCC1)/C=C/C(=O)O] | 1[1,4-oxazepanamido](2E,4E,6E,8E,10E,12E,14E,16Z,18E)-4,8,13,17-tetramethylicosa-2,4,6,8,10,12,14,16,18-nonaenedioate |
| C6 | 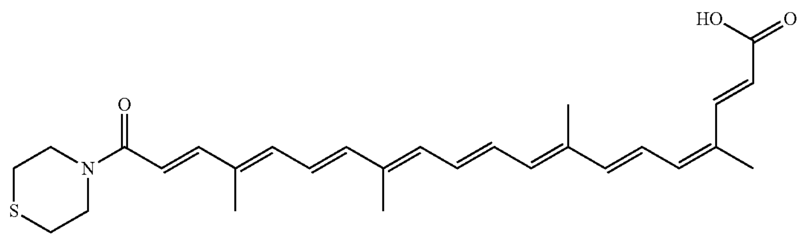 [SMILES: CC(=C/C=C/C(C)=C/C=C/C=C(C)/C=C/C=C(C)/C=C/C(=O)N1CCSCC1)/C=C/C(=O)O] | 1-thiomorpholinamido-(2E,4E,6E,8E,10E,12E,14E,16Z,18E)-4,8,13,17-tetramethylicosa-2,4,6,8,10,12,14,16,18-nonaenedioate |
| C7 | 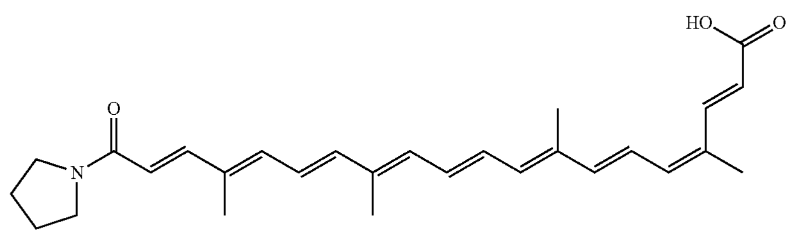 [SMILES: CC(=C/C=C/C(C)=C/C=C/C=C(C)/C=C/C=C(C)/C=C/C(=O)N1CCCC1)/C=C/C(=O)O] | 1-pyrrolidinamido-(2E,4E,6E,8E,10E,12E,14E,16Z,18E)-4,8,13,17-tetramethylicosa-2,4,6,8,10,12,14,16,18-nonaenedioate |
| C8 | 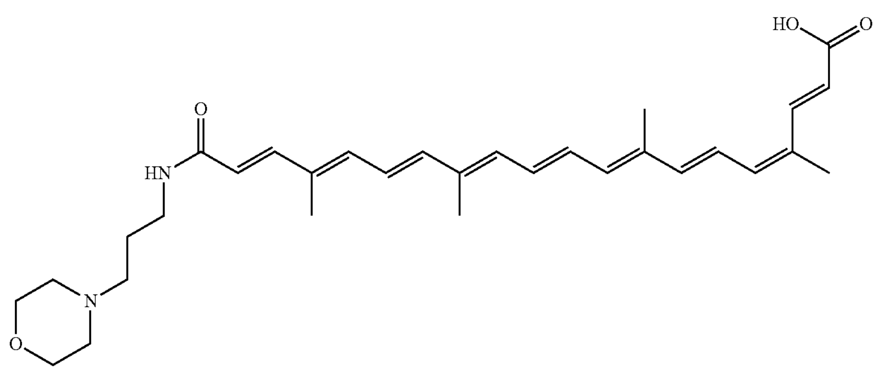 [SMILES: CC(=C/C=C/C(C)=C/C=C/C=C(C)/C=C/C=C(C)/C=C/C(=O)NCCCN1CCOCC1)/C=C/C(=O)O] | 1-[2-morpholinopropanamido](2E,4E,6E,8E,10E,12E,14E,16Z,18E)-4,8,13,17-tetramethylicosa-2,4,6,8,10,12,14,16,18-nonaenedioate |
| C9 | 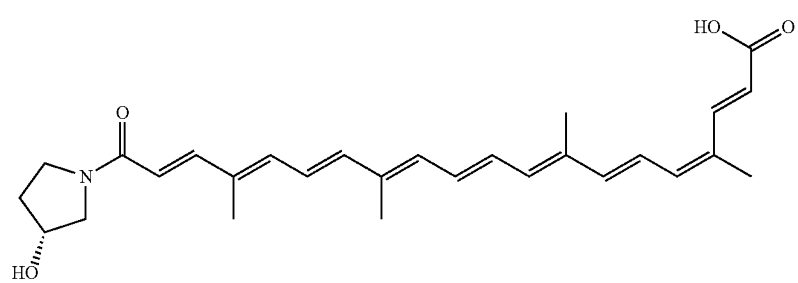 [SMILES: CC(=C/C=C/C(C)=C/C=C/C=C(C)/C=C/C=C(C)/C=C/C(=O)N1CC[C@@H](O)C1)/C=C/C(=O)O] | 1-[(S)-3-hydroxypyrrolidinamido](2E,4E,6E,8E,10E,12E,14E,16Z,18E)-4,8,13,17-tetramethylicosa-2,4,6,8,10,12,14,16,18-nonaenedioate |

TABLE 1-continued

| No | Chemical structure | Chemical name |
|---|---|---|
| C10 | 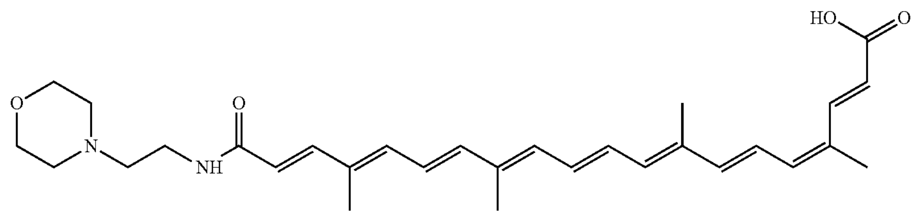 [SMILES: CC(=C/C=C/C(C)=C/C=C/C=C(C)/C=C/C=C(C)/C=C/C(=O)NCCN1CCOCC1)/C=C/C(=O)O] | 1-[2-morpholinoethanamido] (2E,4E,6E,8E,10E,12E, 14E,16Z,18E)-4,8,13,17-tetramethylicosa-2,4,6,8,10,12,14,16,18-nonaenedioate |
| C11 | 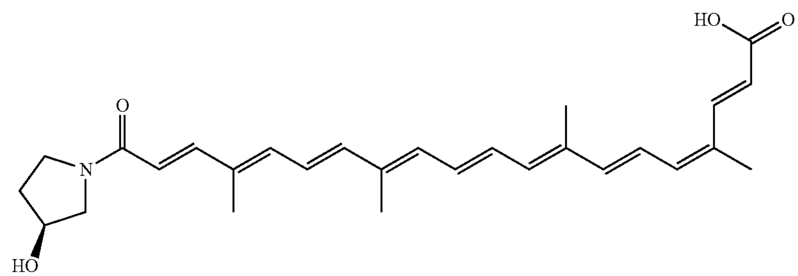 [SMILES: CC(=C/C=C/C(C)=C/C=C/C=C(C)/C=C/C=C(C)/C=C/C(=O)N1CC[C@H](O)C1)/C=C/C(=O)O] | 1-[(R)-3-hydroxypyrrolidinamido] (2E,4E,6E,8E,10E,12E, 14E,16Z,18E)-4,8,13,17-tetramethylicosa-2,4,6,8,10,12,14,16,18-nonaenedioate |
| C12 | 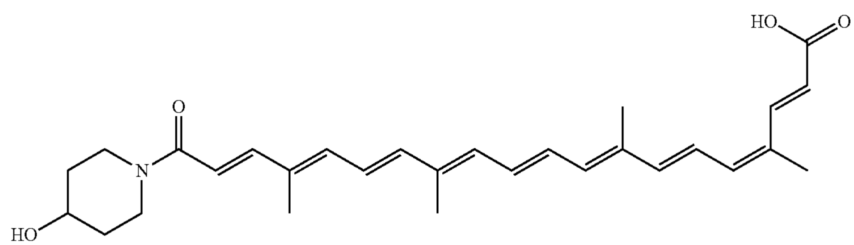 [SMILES: CC(=C/C=C/C(C)=C/C=C/C=C(C)/C=C/C=C(C)/C=C/C(=O)N1CCC(O)CC1)/C=C/C(=O)O] | 1-[4-hydroxypiperidinamido] (2E,4E,6E,8E,10E,12E, 14E,16Z,18E)-4,8,13,17-tetramethylicosa-2,4,6,8,10,12,14,16,18-nonaenedioate |
| C13 | 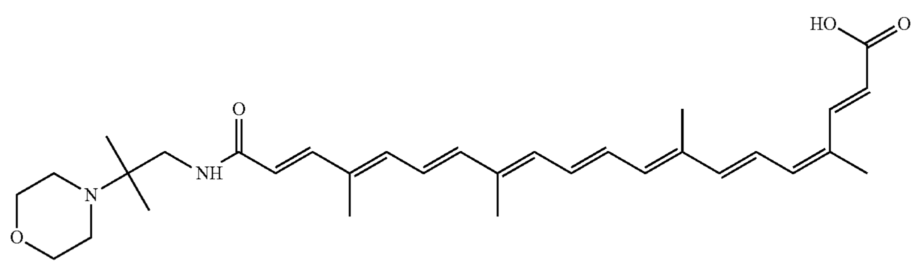 [SMILES: CC(=C/C=C/C(C)=C/C=C/C=C(C)/C=C/C=C(C)/C=C/C(=O)NCC(C)(C)N1CCOCC1)/C=C/C(=O)O] | 1-[2-methyl-2-(4-morpholinyl) propylamido] (2E,4E,6E,8E,10E,12E, 14E,16Z,18E)-4,8,13,17-tetramethylicosa-2,4,6,8,10,12,14,16,18-nonaenedioate |
| C14 | 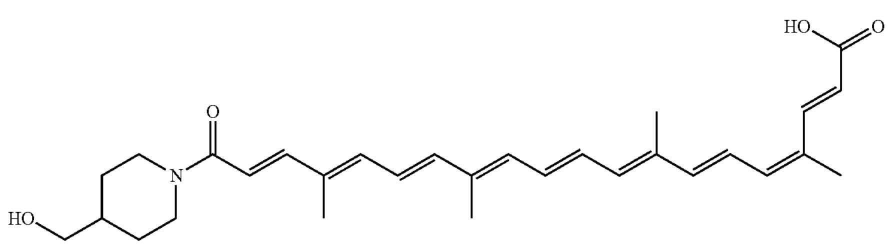 [SMILES: CC(=C/C=C/C(C)=C/C=C/C=C(C)/C=C/C=C(C)/C=C/C(=O)N1CCC(CO)CC1)/C=C/C(=O)O] | 1-[4-hydroxymethyl-piperidinamido] (2E,4E,6E,8E,10E,12E, 14E,16Z,18E)-4,8,13,17-tetramethylicosa-2,4,6,8,10,12,14,16,18-nonaenedioate |
| C15 | 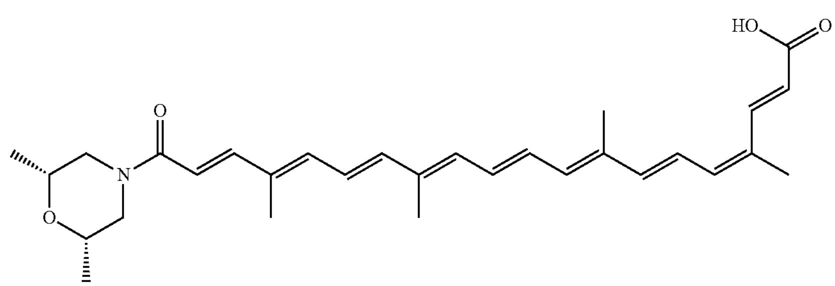 [SMILES: CC(=C/C=C/C(C)=C/C=C/C=C(C)/C=C/C=C(C)/C=C/C(=O)N1C[C@@H](C)O[C@@H](C)C1)/C=C/C(=O)O] | 1-(Z)-3,5-dimethylmorpholinamido] (2E,4E,6E,8E,10E,12E, 14E,16Z,18E)-4,8,13,17-tetramethylicosa-2,4,6,8,10,12,14,16,18-nonaenedioate |

TABLE 1-continued

| No | Chemical structure | Chemical name |
|---|---|---|
| C16 | 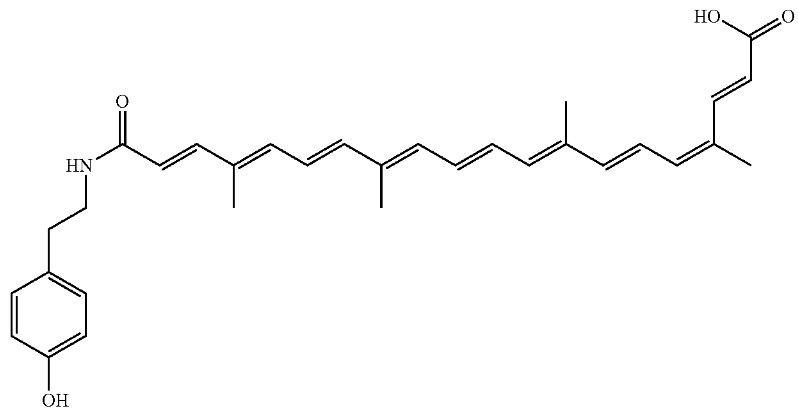 [SMILES: CC(=C/C=C/C(C)=C/C=C/C=C(C)/C=C/C=C(C)/C=C/C(=O)NCCc1ccc(O)cc1)/C=C/C(=O)O] | 1-[4-hydroxyphenyl-ethanamido](2E,4E,6E,8E,10E,12E,14E,16Z,18E)-4,8,13,17-tetramethylicosa-2,4,6,8,10,12,14,16,18-nonaenedioate |
| C17 | 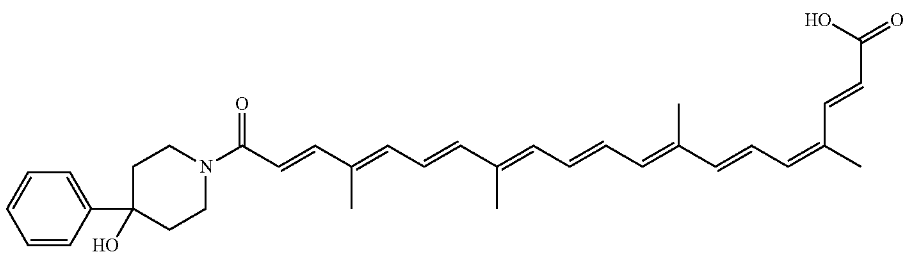 [SMILES: CC(=C/C=C/C(C)=C/C=C/C=C(C)/C=C/C=C(C)/C=C/C(=O)N1CCC(O)(c2ccccc2)CC1)/C=C/C(=O)O] | 1-[4-benzyl-4-hydroxypiperidinamido](2E,4E,6E,8E,10E,12E,14E,16Z,18E)-4,8,13,17-tetramethylicosa-2,4,6,8,10,12,14,16,18-nonaenedioate |
| C18 | 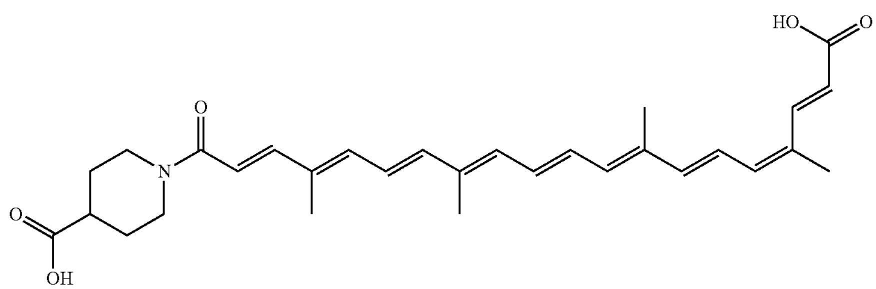 [SMILES: CC(=C/C=C/C(C)=C/C=C/C=C(C)/C=C/C=C(C)/C=C/C(=O)N1CCC(C(=O)O)CC1)/C=C/C(=O)O] | 1-[4-carboxypiperidinamido](2E,4E,6E,8E,10E,12E,14E,16Z,18E)-4,8,13,17-tetramethylicosa-2,4,6,8,10,12,14,16,18-nonaenedioate |
| C19 | 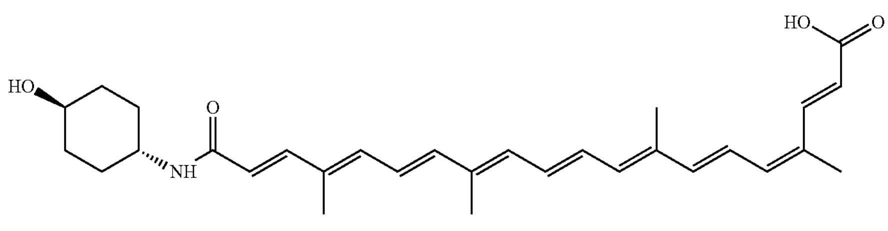 [SMILES: CC(=C/C=C/C(C)=C/C=C/C=C(C)/C=C/C=C(C)/C=C/C(=O)N[C@H]1CC[C@H](O)CC1)/C=C/C(=O)O] | 1-[(E)-4-hydroxycyclohexamido](2E,4E,6E,8E,10E,12E,14E,16Z,18E)-4,8,13,17-tetramethylicosa-2,4,6,8,10,12,14,16,18-nonaenedioate |
| C20 | 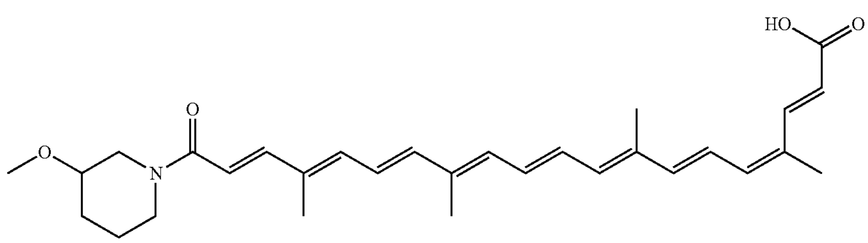 [SMILES: COC1CCCN(C(=O)/C=C/C(C)=C/C=C/C(C)=C/C=C/C=C(C)/C=C/C=C(C)\C=C\C(=O)O)C1] | 1-[3-methoxypiperidinamido](2E,4E,6E,8E,10E,12E,14E,16Z,18E)-4,8,13,17-tetramethylicosa-2,4,6,8,10,12,14,16,18-nonaenedioate |

TABLE 1-continued

| No | Chemical structure | Chemical name |
|---|---|---|
| C21 | 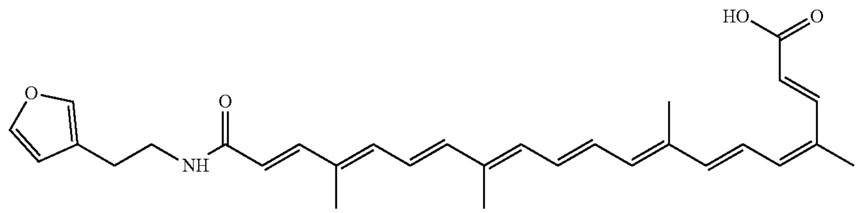 [SMILES: CC(=C/C=C/C(C)=C/C=C/C=C(C)/C=C/C=C(C)/C=C/C(=O)NCCc1ccoc1)/C=C/C(=O)O] | 1-[2-(2-furyl)ethanamido](2E,4E,6E,8E,10E,12E,14E,16Z,18E)-4,8,13,17-tetramethylicosa-2,4,6,8,10,12,14,16,18-nonaenedioate |
| C22 | 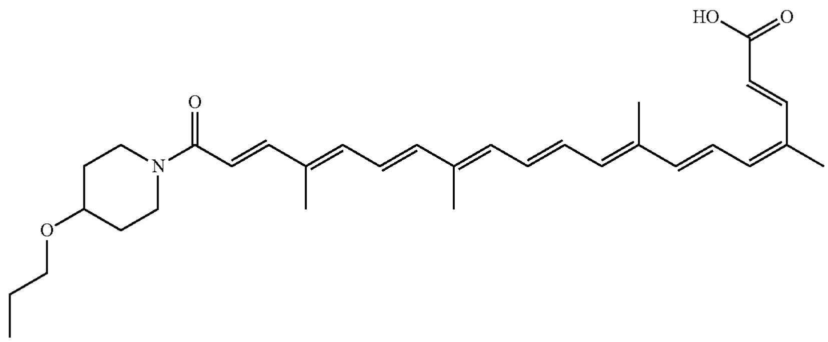 [SMILES: CCCOC1CCN(C(=O)/C=C/C(C)=C/C=C/C(C)=C/C=C/C=C(C)/C=C/C=C(C)\C=C\C(=O)O)CC1] | 1-[4-n-propoxypiperidinamido](2E,4E,6E,8E,10E,12E,14E,16Z,18E)-4,8,13,17-tetramethylicosa-2,4,6,8,10,12,14,16,18-nonaenedioate |
| C23 | 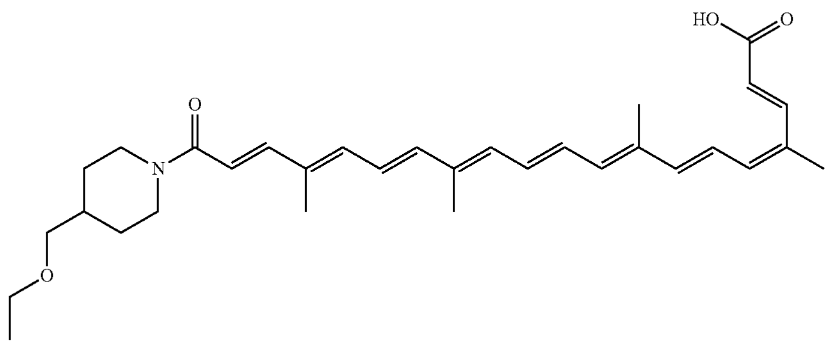 [SMILES: CCOCC1CCN(C(=O)/C=C/C(C)=C/C=C/C(C)=C/C=C/C=C(C)/C=C/C=C(C)\C=C\C(=O)O)CC1] | 1-4-ethylmethoxy-piperidinamido](2E,4E,6E,8E,10E,12E,14E,16Z,18E)-4,8,13,17-tetramethylicosa-2,4,6,8,10,12,14,16,18-nonaenedioate |
| C24 | 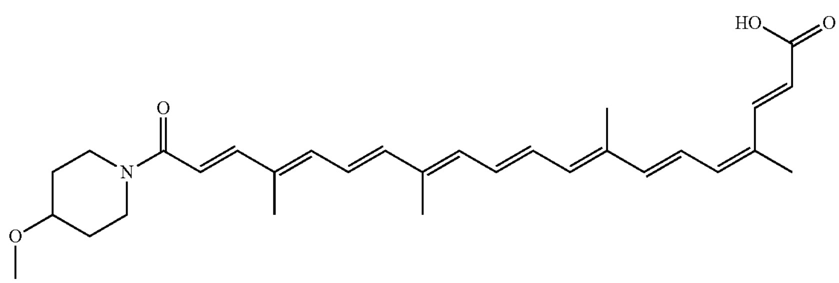 [SMILES: COC1CCN(C(=O)/C=C/C(C)=C/C=C/C(C)=C/C=C/C=C(C)/C=C/C=C(C)\C=C\C(=O)O)CC1] | 1-4-methoxypiperidinamido](2E,4E,6E,8E,10E,12E,14E,16Z,18E)-4,8,13,17-tetramethylicosa-2,4,6,8,10,12,14,16,18-nonaenedioate |

Example 1 (Diagram A)

Preparation of the Compound C21

Step 1 (Typical Coupling Method of an Amine with Carbonyidiimidazole (CDI)): Preparation of the Methyl Ester of C21

The chemical reactions were carried out under argon atmosphere. The reagents and the products were protected from light with aluminum paper during all the steps of the reaction and during the step of extracting and removing solvents. The products were stored at 4° C. The bixin (1 g; 2.54 mmol) is dissolved in 10 mL of dry dimethylformamide (DMF) and triethylamine (1.06 mL; 7.61 mmol) then CDI (0.823 g; 5.07 mmol) are added. After two hours, 2-amino-ethylfuran (845 mg; 7.61 mmol) was added and the reaction mixture was stirred for 18 h at 20° C. Hydrochloric acid (HCl, 1 N; 20 mL) is added and the resulting suspension is centrifuged. Following the removal of the supernatant, the pellet containing the methyl ester was resuspended twice in the presence of water. Following another centrifugation, the pellet (1.24 g) was used directly in the step of hydrolysis.

Step 2 (Typical Procedure of the Hydrolysis): Conversion of the Methyl Ester of C21 into C21

The chemical reactions were carried out under argon atmosphere and protected from light with aluminum paper. The products are stored at 4° C. The methyl ester of C-21 is dissolved in 15 mL of tetrahydrofuran (THF) and 13 mL of MeOH. Sodium hydroxide (NaOH, 1 N; 15.3 mL) is added and the reaction mixture is stirred for 20 h at 20° C. Hydrochloric acid (HCl; 1 N; 16 mL) was added progressively. The suspension obtained is centrifuged and the supernatant is removed. The pellet is then resuspended and mixed twice with water then centrifuged again and the supernatant is removed. The paste obtained, containing water, is transferred to a pyriform flask in the presence of water and acetonitrile, and lyophilized to give 1.04 g of an orangish to red colored powder.

Analyses of the Compound C21

LC-MS: m/z=474.3 (MH$^+$) UV purity at 460 nm=99%.

NMR $^1$H (500 MHz, DMSO-d$_6$) −δ 8.11 (t, 1H), 7.54 (s, 1H), 6.19 (d, 1H), 3.42-3.38 (m, 2H), 2.78 (t, 2H).

Preparation of the Compound C19

Step 1 (Typical Procedure for the Coupling of the Amine by Using HBTU): Preparation of the Methyl Ester of C19 (Method Used for the Preparation of the Methyl Ester of C19 Only, as the Reaction Using CDI is Too Slow for this Compound)

The chemical reactions were carried out under argon atmosphere. The reagents and the products were protected from light with aluminum paper during all the steps of the reaction and during the step of extracting and removing solvents. All the products were stored at 4° C. The bixin (1.17 g; 2.97 mmol) is dissolved in 20 mL of anhydrous DMF and diisopropylamine (1.23 mL; 7.42 mmol); HBTU ((1H-benzotriazol-1-yloxy)-dimethylamino hexafluorophosphate)-N, N'-dimethylmethaniminium; 1.69 g; 4.45 mmol) is then added. After 1 h, trans-4-aminocyclohexanol (680 mg; 4.45 mmol) was added and the reactive mixture is stirred for 18 h at 20° C. Sixty milliliters of water (60 mL) is added and the precipitate was filtered and washed twice with 60 mL of water to give 1.4 g of violet solid compound which is used as is in the step of hydrolysis.

Step 2 (Typical Procedure of the Hydrolysis): Conversion of the Methyl Ester of C19 into C19

The chemical reactions were carried out under argon and protected from light with aluminum paper. The products are stored at 4° C. The 1.4 g of methyl ester of C-21 are dissolved in 10 mL of tetrahydrofuran (THF) and 10 mL of MeOH (dark red solution). Five equivalents of sodium hydroxide (NaOH, 10N; 1.43 mL) are added and the reaction mixture is stirred for 48 h at ambient temperature. In HPLC-MS, a single peak is observed and the absence of starting material. Hydrochloric acid (HCl 12N; 1.18 mL) was added. The precipitate obtained is diluted with 60 mL of water. The solution is centrifuged and the aqueous supernatant is removed. The solid pellet is then taken and mixed with water (30 mL) then centrifuged again and the supernatant is removed. This step is repeated twice until a solid paste of orange color is obtained (which forms a suspension in the presence of water). The solid paste is taken in 50 mL of water to give an orange suspension, frozen and directly lyophilized to give an orange powder (1.02 g).

Analyses of the Compound C19

LC-MS: m/z=478.2 (MH$^+$) UV purity at 460 nm=97.3%.

NMR $^1$H (500 MHz, DMSO-d$_6$) −δ 47.82 (s, 1H), 4.51 (m, 1H), 3.58.-3.53 (m, 1H), 3.40-3.36 (m, 1H), 1.83-1.75 (m, 4H), 1.26-1.15 (m, 4H).

Cascade Screening and Characterization of the Biological Effects of the Chemical Compounds (C) Derived from Norbixin.

The development of the screening test was initiated from work in literature and based on the characteristics of the pathology of dry AMD. At the physiopathologic level, this disease is characterized by a progressive loss of induced vision following the degeneration of the photoreceptors and of the cells of the RPE. The cells of the RPE play a crucial role in the survival and correct operation of the photoreceptors by providing them with the necessary nutrients, by participating in the visual cycle and by removing the debris coming from external segments of photoreceptors and that result from this cycle. It is important to screen the drugs in development on their capacity to target preferably the eye while still avoiding an intraocular administration that is traumatizing for patients and having risks of local infections. To do this, a pharmacokinetic study of the chemical compounds (C) derived from norbixin object of the present invention at the plasma and ocular level was conducted so as to select the chemical compounds having an ocular AUC ("area under the curve") that is improved in relation to norbixin.

In addition to better distribution in the target-tissue, selecting new compounds must also be based on good photo-protective activity that limits the loss of the cells of the RPE and thus reducing the retinal degeneration observed during the AMD and other degenerative diseases such as Retinitis pigmentosa and Stargardt's disease. At the cellular level, on cultures of cells the RPE coming from pig retina, Fontaine et al. (2016) have shown that a treatment with norbixin (BIO201) protects the cells of the RPE against apoptosis following an illumination in the presence of A2E (80% survival 24 h after exposure). This same screening test according to the percentage of photoprotection was used so as to determine its modulation by and the chemical compounds derived from norbixin (C) object of the present invention in comparison with the photo-protective effect of norbixin and characterize these modulations from a statical standpoint.

Protocols

Pharmacokinetic Study Via Oral Administration of the Molecules in Mice

The pharmacokinetic study of the chemical compounds (C) following the oral administration thereof was conducted using mice C57BL/6 (January, 53940 The Genest Saint Isle, France). The chemical compounds derived from norbixin (C) were administered at a dose of 50 mg/kg of body weight. After administration, the blood was sampled at the tail at t=0.25 h; 0.5 h; 1 h; 3 h; 6 h and 8 h. The blood samples were centrifuged and the plasmas taken. The dosage of the plasma samples made it possible to determine pharmacokinetic parameters, namely $C_{max}$, which corresponds to the maximum concentration observed after the administration of the molecule, $T_{max}$ which is the time required to reach maximum concentration after administration of the molecule and the AUC: the area under the curve which corresponds to the plasma exposure (FIG. 2).

In parallel, the ocular concentrations of the chemical compounds derived from norbixin (C) were dosed in the following way (FIG. 1): both eyes of each mouse were taken in Precellys tubes and stored at −80° C. until the time of dosing. The eyes are then ground in the Precellys tubes with a bench homogenizer, Fast-prep (Fischer Scientific, Hampton, United States) in a mixture of organic solvents, in a first step with 500 μL of chloroform/methanol (1/1, v/v) then 500 μL of chloroform/dichloromethane (1/1, v/v). The supernatants are recovered at each step and transferred to a 96-well plate of 2 mL.

For the quantification of the chemical compounds C, a calibration curve is carried out with 8 standards (5 to 5,000 ng/mL) in the same organic solvent mixtures and transferred (100 μL) to the 96-well plate of 2 mL.

The supernatants and standards are evaporated in a EZ2 (Genevac, Ipswich, United Kingdom), without heating, then taken with 100 μL of DMSO/methanol (20:80, v/v) before being transferred to a 96-well plate of 200 μL.

The LC-MSMS analysis is carried out with a HPLC 1200 Infinity chain (Agilent Technologies, Santa-Clara, United States), a UV detector and a mass spectrometer QQQ6420 (Agilent Technologies Santa-Clara, United States). The injection volume is 5 μL. The chemical compounds C are eluted on an inverse phase column C18 (2.1*50 mm, particles 3 μm; Ace-C18-Excel, AIT) with a gradient of acetonitrile and water (containing 0.1% formic acid) and a flow rate of 0.3 mL/min. The conditions of the gradient can change according to the chemical compound C analyzed. The UV detector analyzes at 460 nm and the mass spectrometer analyzed in Mode MRM—Positive.

Photoprotection of the Cells of the RPE

Tests in vitro of photoprotection by the various chemical compounds C of the Cells of the RPE Illuminated in the Presence of A2E The test in vitro described hereinabove and intended to study the photo-protective effect of norbixin was used so as to quantify the photo-protective effects of the various chemical compounds derived from norbixin (C) on the cells of the RPE illuminated with blue light in the presence of A2E (FIG. 3). The photo-protective effect of the molecules was evaluated in a phototoxicity cellular model induced by treatment by A2E followed by an illumination with blue light. The term "blue radiation" means the radiation corresponding to the blue band of the visible light spectrum, i.e. of a wavelength comprised between 435 and 490 nm. This model uses primary cultures of RPE of adult pigs. The cell survival is quantified thanks to a test of cellular viability. At −48 h the compounds to be tested (in solution at 5 mM in the DMSO) are added to obtain the final concentrations of 1 to 20 μM) then at −19 h of the A2E (final concentration 30 μM) and the cells (time 0 h) are illuminated. 24 h after the survival of the cells is measured. The acquisition of images, as well as the processing thereof, are carried out using a fluorescence microscope controlled by the Metamorph software and a dedicated quantification program. The experiments are conducted on a 96-well microplate in quadruplicate and the experiment is reproduced at least four times. The results are expressed in the form of a ratio representing the number of living cells in the wells treated by the molecules to be tested, divided by the number of living cells in the controlled wells (treated by the dilution medium without A2E). This test made it possible hereinabove to reveal the photo-protective activity of norbixin (Fontaine et al. 2016).

Results

Pharmacokinetic Study of the Chemical Compounds C in Mice

Table 2 discloses the pharmacokinetic results of the chemical compounds C following the administration p.o. 50 mg/kg in D-α-Tocopheryl polyethylene glycol 1000 succinate (VitE-TPGS) 20% in a sodium bicarbonate buffer (0.1M).

TABLE 2

| | Eye | | | Plasma | | |
|---|---|---|---|---|---|---|
| | $C_{Max}$ (ng/eye) | $T_{Max}$ (h) | Exposure (ng · h/eye) | $C_{Max}$ (μg/mL) | $T_{Max}$ (h) | Exposure (μg · h/mL) |
| BIO201 | 8.6 | 0.5 | 22.4 | 34.99 | 0.25 | 100.7 |
| C1 | 10.7 | 0.5 | 26.6 | 18.73 | 0.5 | 52.66 |
| C2 | 41 | 0.5 | 186.5 | 34 | 0.5 | 176.2 |
| C3 | 5.1 | 0.5 | 19.1 | 4.05 | 0.5 | 10.37 |
| C4 | 10.2 | 0.5 | 30 | 57.07 | 1 | 208.6 |
| C5 | 31.4 | 0.5 | 188.7 | 37.71 | 1 | 299.9 |
| C6 | 3.9 | 0.5 | 23.1 | 3.95 | 0.5 | 10.81 |
| C7 | 7 | 0.5 | 18.5 | 6.89 | 0.5 | 17.29 |
| C8 | 56.8 | 1 | 472.4 | 59.82 | 0.5 | 173.74 |

TABLE 2-continued

| | Eye | | | Plasma | | |
|---|---|---|---|---|---|---|
| | $C_{Max}$ (ng/eye) | $T_{Max}$ (h) | Exposure (ng · h/eye) | $C_{Max}$ (μg/mL) | $T_{Max}$ (h) | Exposure (μg · h/mL) |
| C9 | 53.1 | 1 | 452 | 37.92 | 1 | 342.68 |
| C10 | 64.3 | 1 | 533.2 | 30.42 | 1 | 108.1 |
| C11 | 47.7 | 1 | 238.4 | 35.91 | 1 | 190 |
| C12 | 50.7 | 1 | 538.4 | 29.31 | 0.5 | 186.3 |
| C13 | 60.7 | 1 | 461.1 | 27.89 | 0.5 | 139.7 |
| C14 | 43.2 | 1 | 322.5 | 19.02 | 0.5 | 162.2 |
| C15 | 22.8 | 0.5 | 108.5 | 17.34 | 0.5 | 46.99 |
| C16 | 7.4 | 0.5 | 8.7 | 10.51 | 1 | 13.23 |
| C17 | 18 | 2 | 135.2 | 8.06 | 1 | 32.39 |
| C18 | 27.7 | 2 | 307.8 | 61.65 | 0.5 | 948.84 |
| C19 | 5.7 | 0.5 | 37.5 | 6.62 | 0.25 | 22.8 |
| C20 | 80.4 | 2 | 421.9 | 35.02 | 1 | 160.4 |
| C21 | 1.6 | 0.25 | 0.6 | 6.61 | 0.25 | 9.17 |
| C22 | 42.1 | 2 | 358.5 | 12.83 | 0.25 | 37.25 |
| C23 | 11 | 2 | 54.7 | 5.01 | 1 | 24.1 |
| C24 | 96 | 1.5 | 499.1 | 48.31 | 0.5 | 141.9 |

Table 3 corresponds to the percentages of photoprotection of the cells of the RPE by the chemical compounds C in vitro: it shows the percentage of cells of RPE surviving in the presence of N-retinyl-N-retinylidene ethanolamine (A2E) and of the various chemical compounds C derived from norbixin (tested at 5, 10 or 20 μM) or of norbixin in the same concentrations after having been subjected to an illumination.

TABLE 3

| | Eye Exposure 50 mg/kg p.o. | Photoprotection (%) | | | | | |
|---|---|---|---|---|---|---|---|
| | AUC | 5 μM | | 10 μM | | 20 μM | |
| | (ng · h/eye) | Mean | SE | Mean | SE | Mean | SE |
| BIO201 | 22.4 | 19.2 | 6.4 | 34.1 | 6.6 | 63.6 | 4.6 |
| C1 | 26.6 | 55.0 | 4.8 | 67.7 | 2.2 | 77.8 | 7.1 |
| C2 | 186.5 | 33.9 | 13.7 | 22.3 | 12.9 | 49.1 | 11.2 |
| C3 | 19.1 | 11.3 | 11.3 | 68.1 | 32.1 | 45.1 | 10.3 |
| C4 | 30.0 | 16.4 | 14.0 | 36.0 | 17.7 | 67.2 | 16.4 |
| C5 | 188.7 | 11.3 | 11.3 | 25.6 | 23.3 | 36.0 | 11.9 |
| C6 | 23.1 | nd | | 60.6 | 30.3 | 19.1 | 19.1 |
| C7 | 18.5 | 5.2 | 5.2 | 52.8 | 14.8 | nd | |
| C8 | 472.4 | 28.6 | 8.4 | 33.4 | 8.2 | 75.2 | 6.7 |
| C9 | 452.0 | 22.1 | 9.4 | 32.0 | 12.7 | 63.7 | 6.1 |
| C10 | 533.2 | 15.5 | 1.1 | 27.4 | 27.4 | 80.3 | 11.4 |
| C11 | 238.4 | 21.1 | 7.7 | 39.3 | 16.7 | 63.4 | 8.2 |
| C12 | 538.4 | 7.7 | 3.1 | 14.3 | 7.6 | 59.6 | 4.3 |
| C13 | 461.1 | 8.0 | 4.0 | 0.5 | 0.3 | 8.0 | 6.5 |
| C14 | 322.5 | 3.1 | 3.1 | 46.8 | 1.2 | 79.3 | 6.0 |
| C15 | 108.5 | 5.4 | 4.0 | 10.0 | 5.1 | 58.5 | 5.7 |
| C16 | 8.7 | 70.2 | 6.1 | 81.7 | 1.6 | 26.8 | 5.6 |
| C17 | 135.2 | 71.7 | 5.4 | 67.2 | 6.4 | 44.0 | 4.9 |
| C18 | 307.8 | 27.3 | 11.7 | 43.1 | 12.4 | 63.8 | 5.9 |
| C19 | 37.5 | 60.6 | 7.5 | 60.6 | 7.5 | 79.9 | 4.1 |
| C20 | 421.9 | 65.6 | 5.7 | 65.6 | 5.7 | 79.0 | 5.4 |
| C21 | 0.6 | 56.7 | 7.0 | 56.7 | 7.0 | 79.6 | 1.1 |
| C22 | 358.5 | 64.5 | 8.2 | 72.8 | 5.7 | 66.0 | 7.9 |
| C23 | 54.7 | 38.4 | 10.4 | 59.2 | 6.8 | 73.1 | 8.3 |
| C24 | 499.1 | 47.0 | 15.0 | 69.0 | 13.0 | 84.0 | 13.6 |

BIBLIOGRAPHY

AREDS Report No. 8. 2001. A randomized, placebo-controlled, clinical trial of high-dose supplementation with vitamins C and E, beta carotene, and zinc for age-related macular degeneration and vision loss. *Arch Ophthalmol*, 119: 1417-1436.

The invention claimed is:

1. Chemical compound having the following general formula (I):

[Chem. 1]

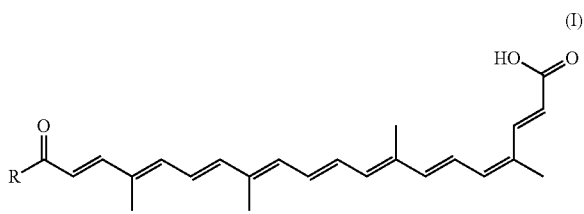

(I)

where COR is a secondary or tertiary amide, such that —R is chosen from:

M; —NH—$(CH_2)_n$-M and —NH—$(CH_2)_n$—$C(CH_3)$ $(CH_3)$-M, -M being chosen from a)

[Chem. 2]

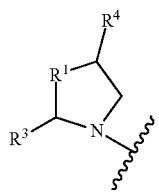

[Chem. 3]

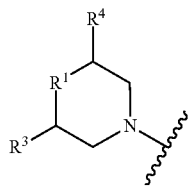

[Chem. 4]

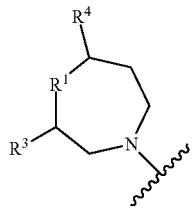

wherein, $R^1$ is chosen from an oxygen atom, a sulfur atom, a >$CH_2$, >CH—O—$(CH_2)_n$—$CH_3$, >CH—$(CH_2)_n$—O—$(CH_2)_n$—$CH_3$, >CH—$(CH_2)_n$—OH, >CH—COOH, >C(OH)phenyl or >NH group;

$R^3$ is chosen from a hydrogen atom, a $C_1$-$C_6$ alkyl, —OH or $C_1$-$C_6$ —O-alkyl group;

$R^4$ is chosen from a hydrogen atom, a $C_1$-$C_6$ alkyl, —OH or $C_1$-$C_6$ —O-alkyl group;

n is an integer comprised between 0 and 6;

—NH—$(CH_2)_n$—W, W being a hydrogen atom, or a —OH group, a —O—$(CH_2)_n$—$CH_3$ group, or a group chosen from i)

[Chem. 5]

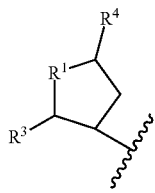

[Chem. 6]

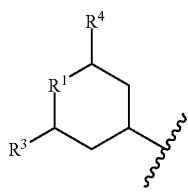

[Chem. 7]

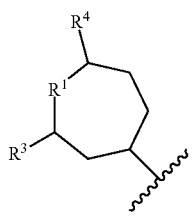

[Chem. 8]

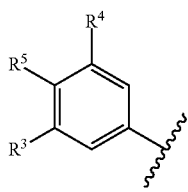

[Chem. 9]

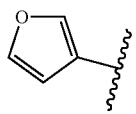

wherein,
$R^1$ is chosen from an oxygen atom, a sulfur atom, a >$CH_2$, >CH—O—$(CH_2)_n$—$CH_3$, >CH—$(CH_2)_n$—OH, >CH—COOH, >C(OH)phenyl or >NH group;
$R^3$ is chosen from a hydrogen atom, a $C_1$-$C_6$ alkyl, —OH or $C_1$-$C_6$ —O-alkyl group;
$R^4$ is chosen from a hydrogen atom, a $C_1$-$C_6$ alkyl, —OH or $C_1$-$C_6$ —O-alkyl group;
$R^5$ is chosen from a —$CH_3$, —OH, —O—$(CH_2)_n$—$CH_3$, —$(CH_2)_n$—OH or —COOH group;
n is an integer comprised between 0 and 6;
as well as the pharmaceutically acceptable salts of said chemical compound.

2. Chemical compound having the general formula (I) according to claim 1, chosen from the following chemical compounds:
1-[2-methoxyethanamido](2E,4E,6E,8E,10E,12E,14E,16Z,18E)-4,8,13,17-tetramethylicosa-2,4,6,8,10,12,14,16,18-nonaenedioate;
1-[1,4-oxazinamido](2E,4E,6E,8E,10E,12E,14E,16Z,18E)-4,8,13,17-tetramethylicosa-2,4,6,8,10,12,14,16,18-nonaenedioate;
1-[piperidinamido](2E,4E,6E,8E,10E,12E,14E,16Z,18E)-4,8,13,17-tetramethylicosa-2,4,6,8,10,12,14,16,18-nonaenedioate;
1-[2-hydoxyethanamido](2E,4E,6E,8E,10E,12E,14E,16Z,18E)-4,8,13,17-tetramethylicosa-2,4,6,8,10,12,14,16,18-nonaenedioate;
1 [1,4-oxazepanamido](2E,4E,6E,8E,10E,12E,14E,16Z,18E)-4,8,13,17-tetramethylicosa-2,4,6,8,10,12,14,16,18-nonaenedioate;
1-thiomorpholinamido-(2E,4E,6E,8E,10E,12E,14E,16Z,18E)-4,8,13,17-tetramethylicosa-2,4,6,8,10,12,14,16,18-nonaenedioate;
1-pyrrolidinamido-(2E,4E,6E,8E,10E,12E,14E,16Z,18E)-4,8,13,17-tetramethylicosa-2,4,6,8,10,12,14,16,18-nonaenedioate;
1-[2-morpholinopropanamido](2E,4E,6E,8E,10E,12E,14E,16Z,18E)-4,8,13,17-tetramethylicosa-2,4,6,8,10,12,14,16,18-nonaenedioate;
1-[(S)-3-hydroxypyrrolidinamido](2E,4E,6E,8E,10E,12E,14E,16Z,18E)-4,8,13,17-tetramethylicosa-2,4,6,8,10,12,14,16,18-nonaenedioate;
1-[2-morpholinoethanamido](2E,4E,6E,8E,10E,12E,14E,16Z,18E)-4,8,13,17-tetramethylicosa-2,4,6,8,10,12,14,16,18-nonaenedioate;
1-[(R)-3-hydroxypyrrolidinamido](2E,4E,6E,8E,10E,12E,14E,16Z,18E)-4,8,13,17-tetramethylicosa-2,4,6,8,10,12,14,16,18-nonaenedioate;
1-[4-hydroxypiperidinamido](2E,4E,6E,8E,10E,12E,14E,16Z,18E)-4,8,13,17-tetramethylicosa-2,4,6,8,10,12,14,16,18-nonaenedioate;
1-[2-methyl-2-(4-morpholinyl) propylamido](2E,4E,6E,8E,10E,12E,14E,16Z,18E)-4,8,13,17-tetramethylicosa-2,4,6,8,10,12,14,16,18-nonaenedioate;
1-[4-hydroxymethylpiperidinamido](2E,4E,6E,8E,10E,12E,14E,16Z,18E)-4,8,13,17-tetramethylicosa-2,4,6,8,10,12,14,16,18-nonaenedioate;
1-[(Z)-2,6-dimethylmorpholinamido](2E,4E,6E,8E,10E,12E,14E,16Z,18E)-4,8,13,17-tetramethylicosa-2,4,6,8,10,12,14,16,18-nonaenedioate;
1-[4-hydroxyphenylamido](2E,4E,6E,8E,10E,12E,14E,16Z,18E)-4,8,13,17-tetramethylicosa-2,4,6,8,10,12,14,16,18-nonaenedioate;
1-[4-benzyl-4-hydroxypiperidinamido](2E,4E,6E,8E,10E,12E,14E,16Z,18E)-4,8,13,17-tetramethylicosa-2,4,6,8,10,12,14,16,18-nonaenedioate;
1-[4-carboxypiperidinamido](2E,4E,6E,8E,10E,12E,14E,16Z,18E)-4,8,13,17-tetramethylicosa-2,4,6,8,10,12,14,16,18-nonaenedioate;
1-[(E)-4-hydroxycyclohexamido](2E,4E,6E,8E,10E,12E,14E,16Z,18E)-4,8,13,17-tetramethylicosa-2,4,6,8,10,12,14,16,18-nonaenedioate;
1-[3-methoxypiperidinamido](2E,4E,6E,8E,10E,12E,14E,16Z,18E)-4,8,13,17-tetramethylicosa-2,4,6,8, 10, 12,14, 16, 18-nonaenedioate;
1-[4-methoxypiperidinamido](2E,4E,6E,8E,10E,12E,14E,16Z,18E)-4,8,13,17-tetramethylicosa-2,4,6,8,10,12,14,16,18-nonaenedioate;
1-[2-(2-furyl)ethanamido](2E,4E,6E,8E,10E,12E,14E,16Z,18E)-4,8,13,17-tetramethylicosa-2,4,6,8,10,12,14,16,18-nonaenedioate;
1-[4-n-propoxypiperidinamido](2E,4E,6E,8E,10E,12E,14E,16Z,18E)-4,8,13,17-tetramethylicosa-2,4,6,8,10,12,14,16,18-nonaenedioate;
1-[4-ethylmethoxypiperidinamido](2E,4E,6E,8E,10E,12E,14E,16Z,18E)-4,8,13,17-tetramethylicosa-2,4,6,8,10,12,14,16,18-nonaenedioate.

3. Composition comprising at least one said chemical compound according to claim 1.

4. The composition according to claim 3 comprising at least one excipient.

5. The composition according to claim 3, comprising a support in a form adapted to be ingested, injected into the eye or injected into the blood.

6. A drug comprising the chemical compound having the general formula (I) according to claim 1.

7. A method for the photoprotection of the cells of the retinal pigment epithelium in mammals, comprising administering to said cells an effective amount of the chemical compound having the general formula (I) of claim 1.

8. A method for the treatment and/or the prevention of damage to the retina of mammals caused by exposure to blue light corresponding to the blue band of the visible light spectrum, of a wavelength comprised between 435 nm and 490 nm, comprising administering an effective amount of the chemical compound having the general formula (I) of claim 1 to a patient in need thereof.

9. A method for the treatment and/or the prevention of damage to the retina of mammals caused by retinal degenerations, comprising administering an effective amount of the chemical compound having the general formula (I) of claim 1 to a patient in need thereof.

10. A method for treatment and/or the prevention of eye diseases in mammals, comprising administering an effective amount of the chemical compound having the general formula (I) of claim 1 to a patient in need thereof.

11. A method for treatment and/or the prevention of retinopathies in mammals, comprising administering an effective amount of the chemical compound having the general formula (I) of claim 1 to a patient in need thereof.

12. A method for treatment and/or the prevention of age-related macular degeneration (AMD) in mammals, comprising administering an effective amount of the chemical compound having the general formula (I) of claim 1 to a patient in need thereof.

13. A method for treatment and/or the prevention of Stargardt's disease and Retinitis pigmentosa in mammals, comprising administering an effective amount of the chemical compound having the general formula (I) of claim 1 to a patient in need thereof.

14. Composition comprising at least one said chemical compound according to claim 2.

15. The composition according to claim 4, comprising a support in a form adapted to be ingested, injected into the eye or injected into the blood.

16. A drug comprising the chemical compound having the general formula (I) according to claim 2.

17. A drug comprising composition of claim 3.

18. A method for the photoprotection of the cells of the retinal pigment epithelium in mammals, comprising administering to said cells an effective amount of the chemical compound having the general formula (I) of claim 2.

19. A method for the photoprotection of the cells of the retinal pigment epithelium in mammals, comprising administering to said cells an effective amount of the composition of claim 3.

20. A method for the treatment and/or the prevention of damage to the retina of mammals caused by exposure to blue light corresponding to the blue band of the visible light spectrum, of a wavelength comprised between 435 nm and 490 nm, comprising administering an effective amount of the chemical compound having the general formula (I) of claim 2 to a patient in need thereof.

\* \* \* \* \*